United States Patent
Braido et al.

(10) Patent No.: US 9,700,409 B2
(45) Date of Patent: Jul. 11, 2017

(54) REDUCED PROFILE PROSTHETIC HEART VALVE

(71) Applicant: St. Jude Medical, Cardiology Division, Inc., St. Paul, MN (US)

(72) Inventors: Peter N. Braido, Wyoming, MN (US); Kent J. Smith, Shoreview, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 14/533,408

(22) Filed: Nov. 5, 2014

(65) Prior Publication Data

US 2015/0127100 A1   May 7, 2015

Related U.S. Application Data

(60) Provisional application No. 61/900,588, filed on Nov. 6, 2013.

(51) Int. Cl.
    *A61F 2/24*   (2006.01)

(52) U.S. Cl.
    CPC .......... *A61F 2/2409* (2013.01); *A61F 2/2412* (2013.01); *A61F 2/2418* (2013.01);
    (Continued)

(58) Field of Classification Search
    CPC .... A61F 2/2412; A61F 2/2418; A61F 2/2409; A61F 2220/0025; A61F 2250/001; A61F 2250/0058
    See application file for complete search history.

(56) References Cited

U.S. PATENT DOCUMENTS

| | | |
|---|---|---|
| 3,657,744 A | 4/1972 | Ersek |
| 4,275,469 A | 6/1981 | Gabbay |
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |

(Continued)

FOREIGN PATENT DOCUMENTS

| | | |
|---|---|---|
| DE | 19857887 A1 | 7/2000 |
| DE | 10121210 A1 | 11/2002 |

(Continued)

OTHER PUBLICATIONS

International Search Report and Written Opinion for Application No. PCT/US2014/063995 dated Feb. 3, 2015.

(Continued)

*Primary Examiner* — Paul Prebilic
(74) *Attorney, Agent, or Firm* — Lerner, David, Littenberg, Krumholz & Mentlik, LLP

(57) ABSTRACT

A prosthetic heart valve may include a stent body with a plurality of cells arranged in circumferential rows and a cuff attached to the stent. A leaflet attachment panel may be attached to and span a portion of one of the cells. A prosthetic valve element, such as a leaflet having a belly, may be mounted to the leaflet attachment panel. The leaflet attachment panel may not be integral with the stent body. A reduced overlap area may be defined between a proximal end of the stent body and a proximalmost point of attachment of the leaflet belly to the cuff. The reduced overlap area may have a size dependent upon the circumferential row of cells the leaflet attachment panel is attached to and a position of the portion of the leaflet attachment panel to which the leaflet is mounted. Alternately, the leaflet may be attached directly to the stent.

21 Claims, 17 Drawing Sheets

(52) U.S. Cl.
CPC . *A61F 2220/005* (2013.01); *A61F 2220/0075* (2013.01); *A61F 2250/0008* (2013.01); *A61F 2250/0062* (2013.01)

(56) References Cited

U.S. PATENT DOCUMENTS

| | | | |
|---|---|---|---|
| 5,480,423 A | 1/1996 | Ravenscroft et al. | |
| 5,843,167 A | 12/1998 | Dwyer et al. | |
| 5,855,601 A | 1/1999 | Bessler et al. | |
| 5,935,163 A | 8/1999 | Gabbay | |
| 5,961,549 A | 10/1999 | Nguyen et al. | |
| 6,045,576 A | 4/2000 | Starr et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,368,348 B1 | 4/2002 | Gabbay | |
| 6,419,695 B1 | 7/2002 | Gabbay | |
| 6,425,916 B1 * | 7/2002 | Garrison | A61F 2/2418 623/1.26 |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,652,578 B2 | 11/2003 | Bailey et al. | |
| 6,685,625 B2 | 2/2004 | Gabbay | |
| 6,716,244 B2 | 4/2004 | Klaco | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 6,951,573 B1 | 10/2005 | Dilling | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,195,641 B2 | 3/2007 | Palmaz et al. | |
| 7,247,167 B2 | 7/2007 | Gabbay | |
| 7,267,686 B2 | 9/2007 | DiMatteo et al. | |
| 7,276,078 B2 | 10/2007 | Spenser et al. | |
| 7,311,730 B2 | 12/2007 | Gabbay | |
| 7,320,704 B2 | 1/2008 | Lashinski et al. | |
| 7,329,278 B2 | 2/2008 | Seguin et al. | |
| 7,374,573 B2 | 5/2008 | Gabbay | |
| 7,381,218 B2 | 6/2008 | Schreck | |
| 7,381,219 B2 | 6/2008 | Salahieh et al. | |
| 7,452,371 B2 | 11/2008 | Pavcnik et al. | |
| 7,510,572 B2 | 3/2009 | Gabbay | |
| 7,510,575 B2 | 3/2009 | Spenser et al. | |
| 7,524,331 B2 | 4/2009 | Birdsall | |
| 7,534,261 B2 | 5/2009 | Friedman | |
| RE40,816 E | 6/2009 | Taylor et al. | |
| 7,585,321 B2 | 9/2009 | Cribier | |
| 7,628,805 B2 | 12/2009 | Spenser et al. | |
| 7,682,390 B2 | 3/2010 | Seguin | |
| 7,708,775 B2 | 5/2010 | Rowe et al. | |
| 7,731,742 B2 | 6/2010 | Schlick et al. | |
| 7,748,389 B2 | 7/2010 | Salahieh et al. | |
| 7,780,725 B2 | 8/2010 | Haug et al. | |
| 7,799,069 B2 | 9/2010 | Bailey et al. | |
| 7,803,185 B2 | 9/2010 | Gabbay | |
| 7,824,442 B2 | 11/2010 | Salahieh et al. | |
| 7,837,727 B2 | 11/2010 | Goetz et al. | |
| 7,846,203 B2 | 12/2010 | Cribier | |
| 7,846,204 B2 | 12/2010 | Letac et al. | |
| 7,892,281 B2 | 2/2011 | Seguin et al. | |
| 7,914,569 B2 | 3/2011 | Nguyen et al. | |
| 7,959,666 B2 | 6/2011 | Salahieh et al. | |
| 7,959,672 B2 | 6/2011 | Salahieh et al. | |
| 7,972,378 B2 | 7/2011 | Tabor et al. | |
| 7,988,724 B2 | 8/2011 | Salahieh et al. | |
| 7,993,394 B2 | 8/2011 | Hariton et al. | |
| 8,016,877 B2 | 9/2011 | Seguin et al. | |
| D648,854 S | 11/2011 | Braido | |
| 8,048,153 B2 | 11/2011 | Salahieh et al. | |
| 8,052,741 B2 | 11/2011 | Bruszewski et al. | |
| 8,052,749 B2 | 11/2011 | Salahieh et al. | |
| 8,052,750 B2 | 11/2011 | Tuval et al. | |
| 8,062,355 B2 | 11/2011 | Figulla et al. | |
| 8,075,611 B2 | 12/2011 | Millwee et al. | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| 8,137,398 B2 | 3/2012 | Tuval et al. | |
| 8,142,497 B2 | 3/2012 | Friedman | |
| D660,432 S | 5/2012 | Braido | |
| D660,433 S | 5/2012 | Braido et al. | |
| D660,967 S | 5/2012 | Braido et al. | |
| 8,182,528 B2 | 5/2012 | Salahieh et al. | |
| 8,221,493 B2 | 7/2012 | Boyle et al. | |
| 8,230,717 B2 | 7/2012 | Matonick | |
| 8,231,670 B2 | 7/2012 | Salahieh et al. | |
| 8,252,051 B2 | 8/2012 | Chau et al. | |
| 8,308,798 B2 | 11/2012 | Pintor et al. | |
| 8,313,525 B2 | 11/2012 | Tuval et al. | |
| 8,323,335 B2 | 12/2012 | Rowe et al. | |
| 8,323,336 B2 | 12/2012 | Hill et al. | |
| 8,343,213 B2 | 1/2013 | Salahieh et al. | |
| 8,348,995 B2 | 1/2013 | Tuval et al. | |
| 8,348,996 B2 | 1/2013 | Tuval et al. | |
| 8,348,998 B2 | 1/2013 | Pintor et al. | |
| 8,366,769 B2 | 2/2013 | Huynh et al. | |
| 8,403,983 B2 | 3/2013 | Quadri et al. | |
| 8,408,214 B2 | 4/2013 | Spenser | |
| 8,414,643 B2 | 4/2013 | Tuval et al. | |
| 8,425,593 B2 | 4/2013 | Braido et al. | |
| 8,449,599 B2 | 5/2013 | Chau et al. | |
| 8,449,604 B2 | 5/2013 | Moaddeb et al. | |
| 8,454,686 B2 | 6/2013 | Alkhatib | |
| 8,500,798 B2 | 8/2013 | Rowe et al. | |
| 8,568,474 B2 | 10/2013 | Yeung et al. | |
| 8,579,962 B2 | 11/2013 | Salahieh et al. | |
| 8,579,966 B2 | 11/2013 | Seguin et al. | |
| 8,585,755 B2 | 11/2013 | Chau et al. | |
| 8,591,575 B2 | 11/2013 | Cribier | |
| 8,597,349 B2 | 12/2013 | Alkhatib | |
| 8,603,159 B2 | 12/2013 | Seguin et al. | |
| 8,603,160 B2 | 12/2013 | Salahieh et al. | |
| 8,613,765 B2 | 12/2013 | Bonhoeffer et al. | |
| 8,623,074 B2 | 1/2014 | Ryan | |
| 8,652,204 B2 | 2/2014 | Quill et al. | |
| 8,663,322 B2 | 3/2014 | Keranen | |
| 8,668,733 B2 | 3/2014 | Haug et al. | |
| 8,685,080 B2 | 4/2014 | White | |
| 8,728,154 B2 | 5/2014 | Alkhatib | |
| 8,747,459 B2 | 6/2014 | Nguyen et al. | |
| 8,764,820 B2 | 7/2014 | Dehdashtian et al. | |
| 8,795,357 B2 | 8/2014 | Yohanan et al. | |
| 8,801,776 B2 | 8/2014 | House et al. | |
| 8,808,356 B2 | 8/2014 | Braido et al. | |
| 8,828,078 B2 | 9/2014 | Salahieh et al. | |
| 8,834,563 B2 | 9/2014 | Righini | |
| 8,840,663 B2 | 9/2014 | Salahieh et al. | |
| 8,876,894 B2 | 11/2014 | Tuval et al. | |
| 8,876,895 B2 | 11/2014 | Tuval et al. | |
| 8,940,040 B2 | 1/2015 | Shahriari | |
| 8,945,209 B2 | 2/2015 | Bonyuet et al. | |
| 8,961,595 B2 | 2/2015 | Alkhatib | |
| 8,974,523 B2 | 3/2015 | Thill et al. | |
| 8,974,524 B2 | 3/2015 | Yeung et al. | |

(56) References Cited

U.S. PATENT DOCUMENTS

| | | |
|---|---|---|
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0111111 A1 | 6/2004 | Lin |
| 2004/0210304 A1 | 10/2004 | Seguin et al. |
| 2004/0260389 A1 | 12/2004 | Case et al. |
| 2005/0096726 A1 | 5/2005 | Sequin et al. |
| 2005/0137682 A1 | 6/2005 | Justino |
| 2005/0137695 A1 | 6/2005 | Salahieh et al. |
| 2005/0137697 A1 | 6/2005 | Salahieh et al. |
| 2005/0203605 A1 | 9/2005 | Dolan |
| 2005/0256566 A1 | 11/2005 | Gabbay |
| 2006/0008497 A1 | 1/2006 | Gabbay |
| 2006/0058872 A1 | 3/2006 | Salahieh et al. |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0161249 A1 | 7/2006 | Realyvasquez et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0276027 A1 | 11/2009 | Glynn |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0264206 A1 | 10/2011 | Tabor |
| 2012/0035722 A1 | 2/2012 | Tuval |
| 2012/0078347 A1 | 3/2012 | Braido et al. |
| 2012/0101572 A1 | 4/2012 | Kovalsky et al. |
| 2012/0123529 A1 | 5/2012 | Levi et al. |
| 2012/0303116 A1 | 11/2012 | Gorman, III et al. |
| 2013/0018458 A1 | 1/2013 | Yohanan et al. |
| 2013/0261740 A1 | 10/2013 | Eberhardt et al. |
| 2013/0274873 A1 | 10/2013 | Delaloye et al. |
| 2014/0121763 A1 | 5/2014 | Duffy et al. |
| 2014/0155997 A1 | 6/2014 | Braido |
| 2014/0214159 A1 | 7/2014 | Vidlund et al. |
| 2014/0228946 A1 | 8/2014 | Chau et al. |
| 2014/0277417 A1* | 9/2014 | Schraut .......... A61F 2/2403 623/2.17 |
| 2014/0303719 A1 | 10/2014 | Cox et al. |
| 2014/0324164 A1 | 10/2014 | Gross et al. |
| 2014/0343671 A1 | 11/2014 | Yohanan et al. |
| 2014/0350668 A1 | 11/2014 | Delaloye et al. |
| 2014/0350669 A1 | 11/2014 | Gillespie et al. |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 1926455 A2 | 6/2008 |
| EP | 2537487 A1 | 12/2012 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 2006073626 A2 | 7/2006 |
| WO | 2007053243 A2 | 5/2007 |
| WO | 2007071436 A2 | 6/2007 |
| WO | 2008070797 A2 | 6/2008 |
| WO | 2009042196 A2 | 4/2009 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |
| WO | 2011120050 A1 | 9/2011 |
| WO | 2012161786 A1 | 11/2012 |

OTHER PUBLICATIONS

Zegdi, Rachid, MD, PhD et al., "Is It Reasonable to Treat All Calcified Stenotic Aortic Valves With a Valved Stent?" 579-584, J. of the American College of Cardiology, vol. 51, No. 5, Feb. 5, 2008.

(56) References Cited

OTHER PUBLICATIONS

Ruiz, Carlos, Overview of PRE-CE Mark Transcatheter Aortic Valve Technologies, Euro PCR (powerpoint—dated May 25, 2010).
U.S. Appl. No. 29/375,243, filed Sep. 20, 2010.
U.S. Appl. No. 29/375,260, filed Sep. 20, 2010.
78. Heart repairs without surgery. Minimally invasive procedures aim to correct valve leakage. PubMed ID 15586429, Heart Advisor, Sep. 2004.
Kodali, Susheel K. et al., "Two-Year Outcomes after Transcatheter or Surgical Aortic-Valve Replacement", The New England Journal of Medicine, downloaded from <http://researchonline.Ishtm.ac.uk/20681/>, pp. 1686-1695, May 3, 2012.
Sinning et al., "Aortic Regurgitation Index Defines Severity of Peri-Prosthetic Regurgitation and Predicts Outcome in Patients After Transcatheter Aortic Valve Implantation", Journal of the American College of Cardiology, vol. 59, No. 13, pp. 1134-1141, Mar. 27, 2012.
U.S. Appl. No. 61/900,475, filed Nov. 6, 2013, (declaration only).

\* cited by examiner

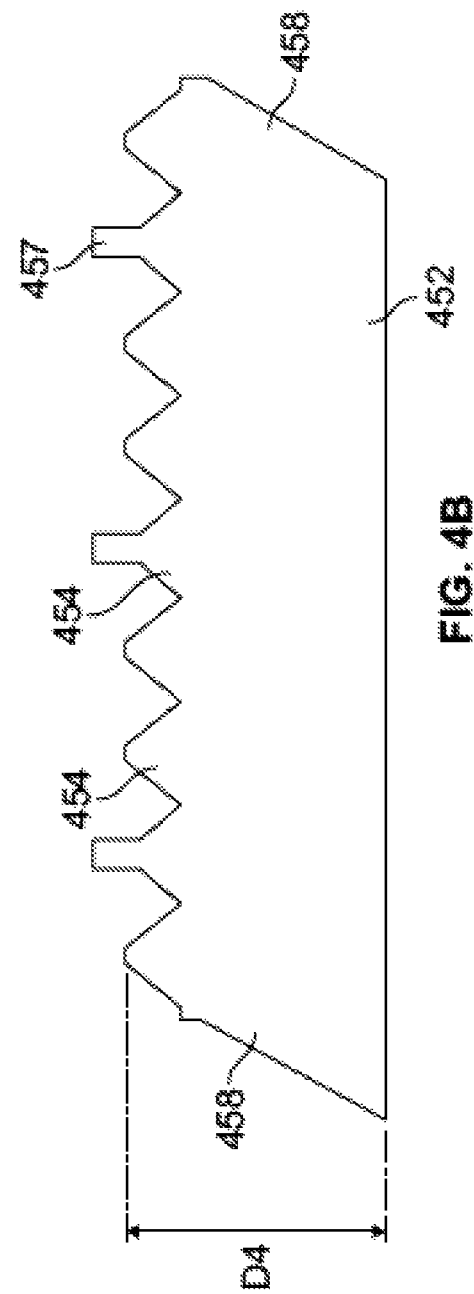

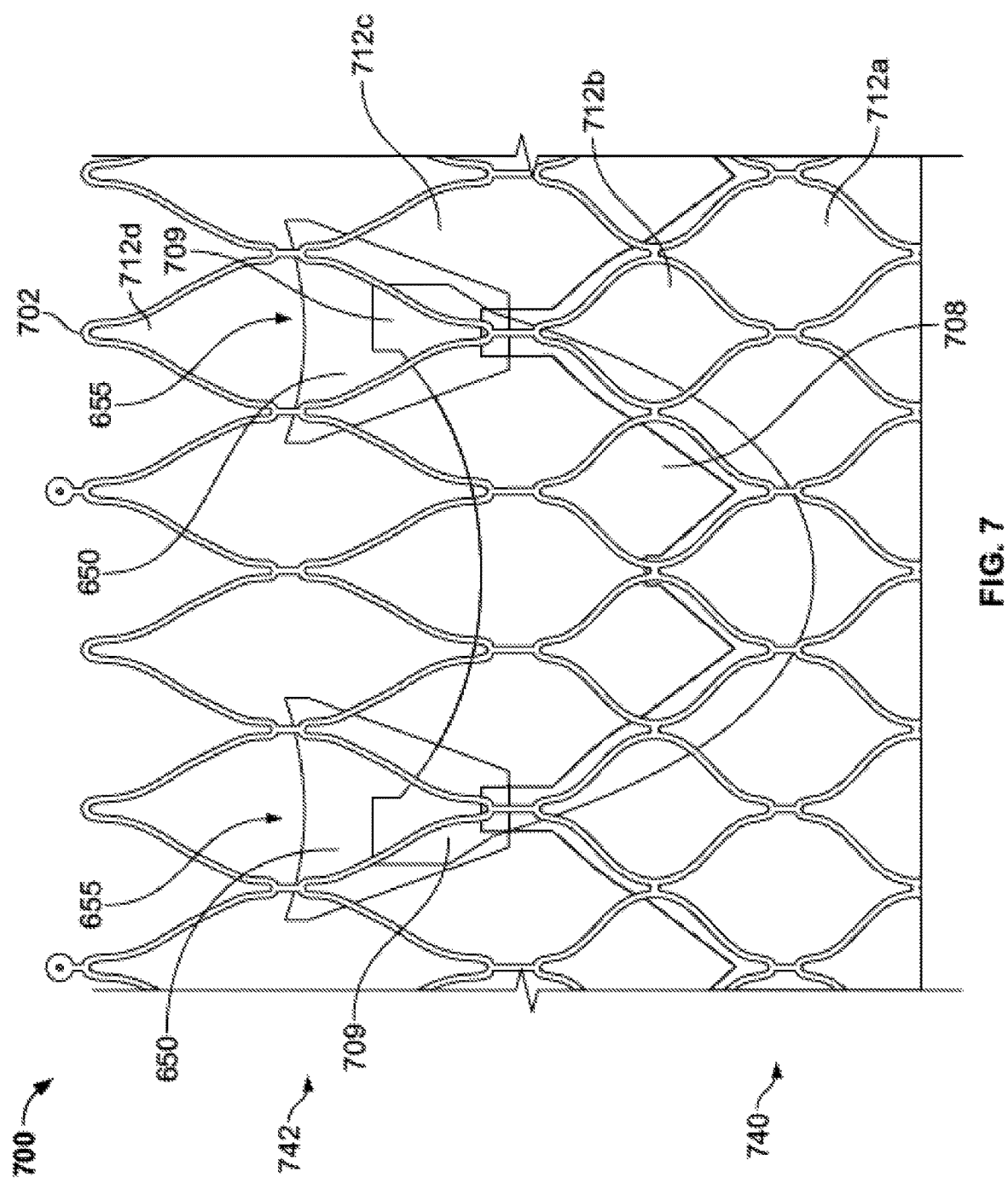

REDUCED PROFILE PROSTHETIC HEART VALVE

CROSS-REFERENCE TO RELATED APPLICATIONS

The present application claims the benefit of the filing date of U.S. Provisional Patent Application No. 61/900,588, filed Nov. 6, 2013, the disclosure of which is hereby incorporated by reference herein.

BACKGROUND

The present disclosure relates to heart valve replacement and, in particular, to collapsible prosthetic heart valves. More particularly, the present disclosure relates to collapsible prosthetic heart valves having designs that facilitate the inclusion of additional features, such as paravalvular leak ("PV leak") mitigation features.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the valve, assuring its proper location, and then expanding a balloon positioned within the valve stent. For self-expanding valves, on the other hand, the stent automatically expands as the sheath covering the valve is withdrawn.

Clinical success of a collapsible prosthetic heart valve may be dependent on accurate deployment and sealing. For example, inaccurate deployment and anchoring may result in the leakage of blood between the implanted heart valve and the native valve annulus, commonly referred to as perivalvular or paravalvular leakage ("PV leak"). In aortic valves, this leakage enables blood to flow from the aorta back into the left ventricle, which can reduce cardiac efficiency and put a greater strain on the heart muscle. Additionally, calcification of the aortic valve may affect performance and the interaction between the implanted valve and the calcified tissue is believed to be relevant to leakage. Additionally, in certain procedures, collapsible valves may be implanted in a native valve annulus without first resecting the native valve leaflets.

Adding features to a prosthetic heart valve to help mitigate PV leak may result in the profile of the valve increasing in size. Increasing the profile of the valve may be undesirable, for example, because delivering the valve may require a correspondingly larger delivery device. Similarly, adding features to a prosthetic valve has a potential of adversely impacting other design factors, such as hemodynamic performance, durability, and sealing.

BRIEF SUMMARY

In one aspect, the present disclosure relates, at least in part, to prosthetic heart valves having features that reduce the profile of the valves and that otherwise increase the available space on the valve for attaching additional features, such as PV leak mitigation features. For example, if a PV leak mitigation (or other) feature is added to a prosthetic heart valve, the profile of the prosthetic valve may increase. However, methods and apparatus disclosed herein may help reduce the profile of the prosthetic valve to partially or completely offset the increase in profile resulting from the addition of additional valve features. A number of other benefits may also be obtained from the disclosure provided herein.

In one embodiment of the disclosure, a prosthetic heart valve includes a stent body having a plurality of cells arranged in circumferential rows and a cuff attached to the stent body. At least one leaflet attachment panel may be attached to and may span at least a portion of one of the cells. At least one prosthetic valve element may be mounted to the at least one leaflet attachment panel, and the leaflet attachment panel may not be integral with the stent body.

In another embodiment of the disclosure, a prosthetic heart valve includes a stent body having a proximal end, a distal end, and including a plurality of cells arranged in a plurality of circumferential rows. A cuff may be attached to the stent body. A leaflet attachment panel may be attached to at least one cell in one of the circumferential rows. A leaflet may be mounted to a portion of the leaflet attachment panel, the leaflet including a leaflet belly having a proximalmost point of attachment to the cuff. A reduced overlap area may be defined between the proximal end of the stent body and the proximalmost point of attachment of the leaflet belly to the cuff, the reduced overlap area having a size. The size of the reduced overlap area may be dependent upon (i) the circumferential row of cells the leaflet attachment panel is attached to and (ii) a position of the portion of the leaflet attachment panel to which the leaflet is mounted.

In yet a further embodiment of the disclosure, a prosthetic heart valve includes a stent body having a plurality of cells arranged in circumferential rows and a plurality of strut intersections defined by an intersection of at least two adjacent cells. A cuff may be attached to the stent body. A portion of a first leaflet may be attached directly to one of the plurality of strut intersections. A portion of a second leaflet may be attached directly to the one of the plurality of strut intersections.

In still another embodiment of the disclosure, a prosthetic heart valve includes a stent body having a proximal end and a distal end, the stent body formed from a plurality of open cells arranged in circumferential rows, and a cuff attached to the stent body. A leaflet attachment panel may be attached to and may overlie at least a portion of one of the open cells, the leaflet attachment panel having a proximal end and a distal end. A leaflet may be attached to a portion of the leaflet attachment panel between the proximal end and the distal end thereof, the leaflet including a leaflet belly having a proximalmost point of attachment to the cuff. An area between the proximal end of the stent body and the proximalmost point of attachment of the leaflet belly to the cuff may define a reduced overlap area having a longitudinal length. The longitudinal length of the reduced overlap area may be at least dependent upon a location of attachment of the leaflet to the leaflet attachment panel between the proximal end and distal end thereof.

BRIEF DESCRIPTION OF THE DRAWINGS

FIG. 4B is a front plan view of the cuff of FIG. 4A.

FIG. 7 is a schematic view of the circumference of a prosthetic heart valve laid flat out, according to still another embodiment of the disclosure.

DETAILED DESCRIPTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. The term "circumferential," when used in connection with a prosthetic heart valve, refers to the direction around the perimeter of the valve. The term "leading end," when used in connection with a suture, refers to the end initially advanced through a material, while the term "trailing end" refers to the opposite end.

Figure 1A:
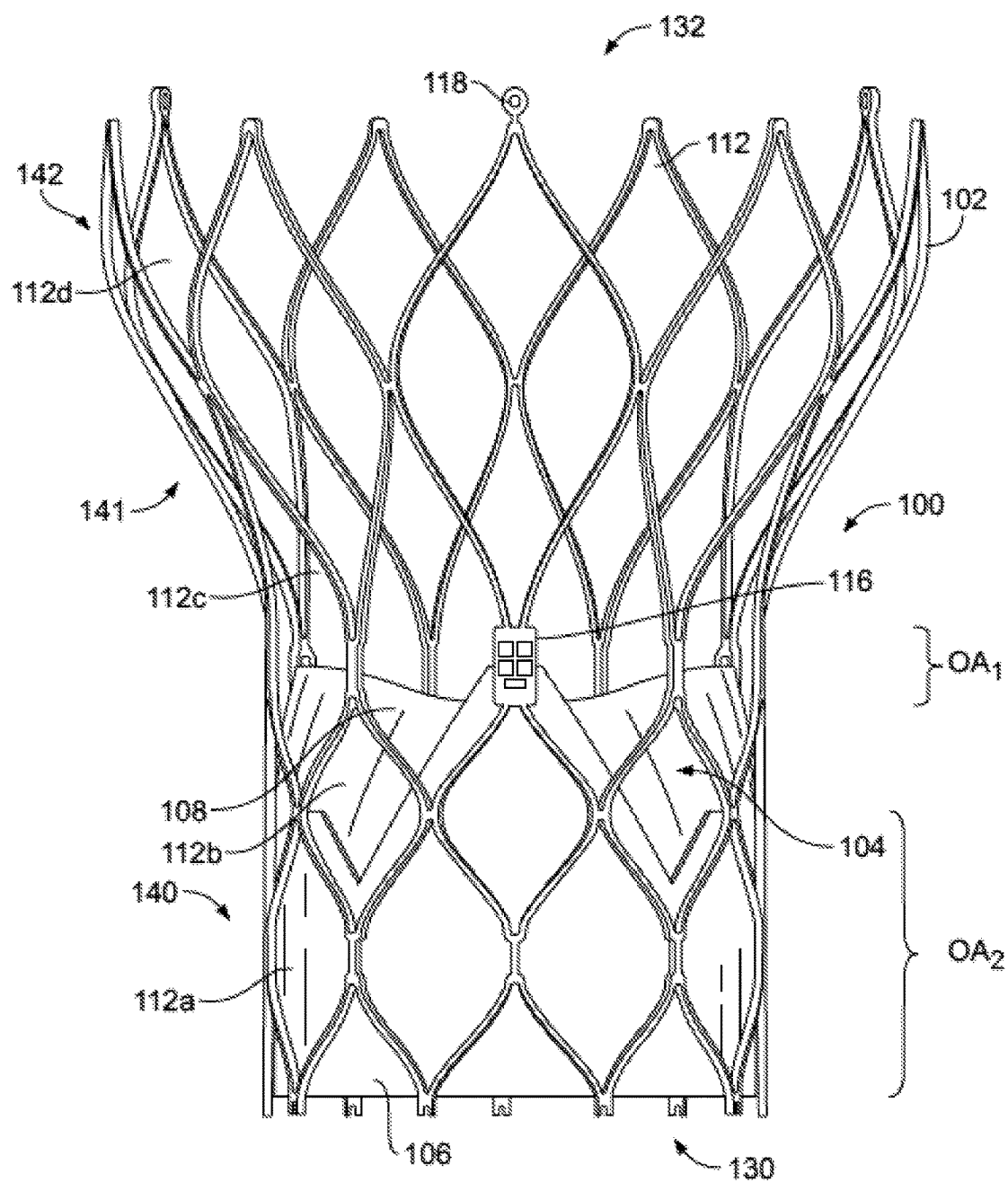
FIG. 1A is a side elevational view of a conventional prosthetic heart valve.

FIG. 1A shows a collapsible stent-supported prosthetic heart valve 100 known in the art. The prosthetic heart valve 100 is designed to replace the function of a native tricuspid, bicuspid or unicuspid valve of a patient, such as a native aortic valve. It should be noted that while the present disclosure is described predominately in connection with prosthetic aortic valves and a stent having a shape as illustrated in FIG. 1A, the concepts described herein may also be used with prosthetic bicuspid valves, such as for a mitral valve replacement, and with stents having different shapes, such as those having a flared or conical annulus section, a less-bulbous aortic section, and the like, and a differently shaped transition section. Examples of collapsible prosthetic heart valves are described in International Patent Application Publication No. WO/2009/042196; U.S. Pat. No. 7,018,406; and U.S. Pat. No. 7,329,278, the disclosures of all of which are hereby incorporated herein by reference.

Prosthetic heart valve 100 will be described in more detail with reference to FIG. 1A. Prosthetic heart valve 100 includes expandable stent 102, which may be formed from biocompatible materials that are capable of self-expansion, such as, for example, shape memory alloys such as nitinol. Stent 102 extends from proximal or annulus end 130 to a distal or aortic end 132, and includes tubular annulus section 140 adjacent the proximal end and aortic section 142 adjacent the distal end. Annulus section 140 has a relatively small cross-section in the expanded condition, while aortic section 142 has a relatively large cross-section in the expanded condition. Preferably, annulus section 140 is in the form of a cylinder having a substantially constant diameter along its length. Transition section 141 may taper outwardly from annulus section 140 to aortic section 142. Each of the sections of stent 102 includes a plurality of cells 112 connected to one another in one or more annular rows around the stent. For example, as shown in FIG. 1A, annulus section 140 may define a first proximalmost circumferential row of cells 112a and a second circumferential row of cells 112b positioned distal to the first row of cells. Aortic section 142 may also define a circumferential row of cells 112d, which may be the distalmost cells. An intermediate circumferential row of cells 112c may be positioned between the proximalmost row of cells 112a and the distalmost row of cells 112d. Cells 112d in aortic section 142 may be larger than the cells 112a, 112b in annulus section 140. The larger cells in aortic section 142 better enable prosthetic valve 100 to be positioned in the native valve annulus without the stent structure interfering with blood flow to the coronary arteries.

Stent 102 may include one or more retaining elements 118 at distal end 132 thereof, the retaining elements being sized and shaped to cooperate with retaining structures provided on the deployment device (not shown). The engagement of retaining elements 118 with retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed. In some variations, retaining elements 118 may be disposed near proximal end 130 of heart valve 100.

Prosthetic heart valve 100 includes a valve assembly 104, preferably positioned in the annulus section 140 of stent 102 and secured to the stent. Valve assembly 104 may include cuff 106 and a plurality of prosthetic valve elements, such as leaflets 108, which collectively function as a one-way valve by coapting with one another, generally allowing blood to flow in an antegrade direction while substantially blocking blood from flowing in a retrograde direction. As a prosthetic aortic valve, valve 100 has three leaflets 108. However, it will be appreciated that other prosthetic heart valves with which the present disclosure may be used may have a more or fewer leaflets.

Although cuff 106 is shown in FIG. 1A as being disposed on the luminal or inner surface of annulus section 140, it is contemplated that the cuff may be disposed on the abluminal or outer surface of the annulus section or may cover all or part of either or both of the luminal and abluminal surfaces. Both cuff 106 and leaflets 108 may be wholly or partly formed of any suitable biological material or polymer such as, for example, PTFE.

Leaflets 108 may be attached along their belly portions to cells 112 of stent 102, with the commissure between adjacent leaflets attached to commissure attachment features ("CAFs") 116. As can be seen in FIG. 1A, each CAF 116 may lie at the intersection of four cells 112 of stent 102, two of the cells being adjacent one another in the same annular row, and the other two cells being in different annular rows and lying in end-to-end relationship. Preferably, CAFs 116 are positioned entirely within the annulus section 140 of stent 102 or at the juncture of annulus section 140 and transition section 141, although they may be positioned above the annulus section. CAFs 116 may include one or more eyelets which facilitate the suturing of the leaflet commissure to the stent.

In the illustrated embodiment, CAFs 116 are formed by stent body 102, or, in other words, are unitary or integral with the stent body. This may be achieved by, for example, laser cutting the stent body 102, including CAFs 116, from a single piece of material. CAFs 116 may add to the profile of valve 100 compared to an identical valve without the CAFs. CAFs 116 may also reduce the ability of stent body 102 to bend to match the anatomy during delivery, such as when the valve 100 is delivered through the aortic arch. This ability to bend or otherwise conform to the anatomy may be referred to as tracking ability. Because of their relative stiffness compared to the remainder of stent 102, CAFs 116 may also raise the likelihood of vessel trauma or particulate dislodgement, which may result in problems such as stroke. However, if CAFs 116 are not included in stent body 102, another method of attachment leaflets to the stent may be required.

Prosthetic heart valve 100 may be used to replace, for example, a native aortic valve, a surgical heart valve, a repair device or a heart valve that has undergone a surgical procedure. The prosthetic heart valve may be delivered to the desired site (e.g., near the native aortic annulus) using any suitable delivery device. During delivery, the prosthetic heart valve is disposed inside the delivery device in the collapsed condition. The delivery device may be introduced into a patient using a transfemoral, transapical, transseptal, transaortic, subclavian, or any other percutaneous approach. Once the delivery device has reached the target site, the user may deploy prosthetic heart valve 100. Upon deployment, prosthetic heart valve 100 expands so that annulus section 140 is in secure engagement within the native aortic annulus. When the prosthetic heart valve is properly positioned inside the heart, it works as a one-way valve, allowing blood to flow from the left ventricle of the heart to the aorta, and preventing blood from flowing in the opposite direction.

As discussed above, adding features, such as PV leak mitigation features, may increase the profile of a typical valve. Such a PV leak mitigation feature may take the form of, for example, those described in U.S. Patent Publication No. 2011/0098802, or the parachute-like sealing members described in U.S. Provisional Patent Application No. 61/900,475, titled "PARAVALVULAR LEAK SEALING MECHANISM" and filed on Nov. 6, 2013, the entire contents of both of which are hereby incorporated by reference herein. However, areas of valve 100 may already have a significant amount of overlap of material, causing the profile to be relatively large. Such areas of overlap are indicated in FIG. 1A as first overlap area $OA_1$ where CAFs 116 are positioned and second overlap area $OA_2$, where cuff 106, stent body 102, and leaflets 108 overlap. A number of designs are discussed below that allow PV leak mitigation and other features to be added to a valve without increasing, or only minimally increasing, the profile of the valve. For example, by rearranging the placement of leaflets and the cuff, areas of overlap between the leaflet and cuff may be reduced. This may allow a feature to be added onto the cuff such that there are few or no points in which all three of the cuff, the leaflet, and the additional feature overlap. This may result in a smaller valve profile. In addition, removal of a traditional CAF from the valve may reduce the profile of the valve, allowing other features to be added without significantly changing the profile of the valve.

Figure 1B:
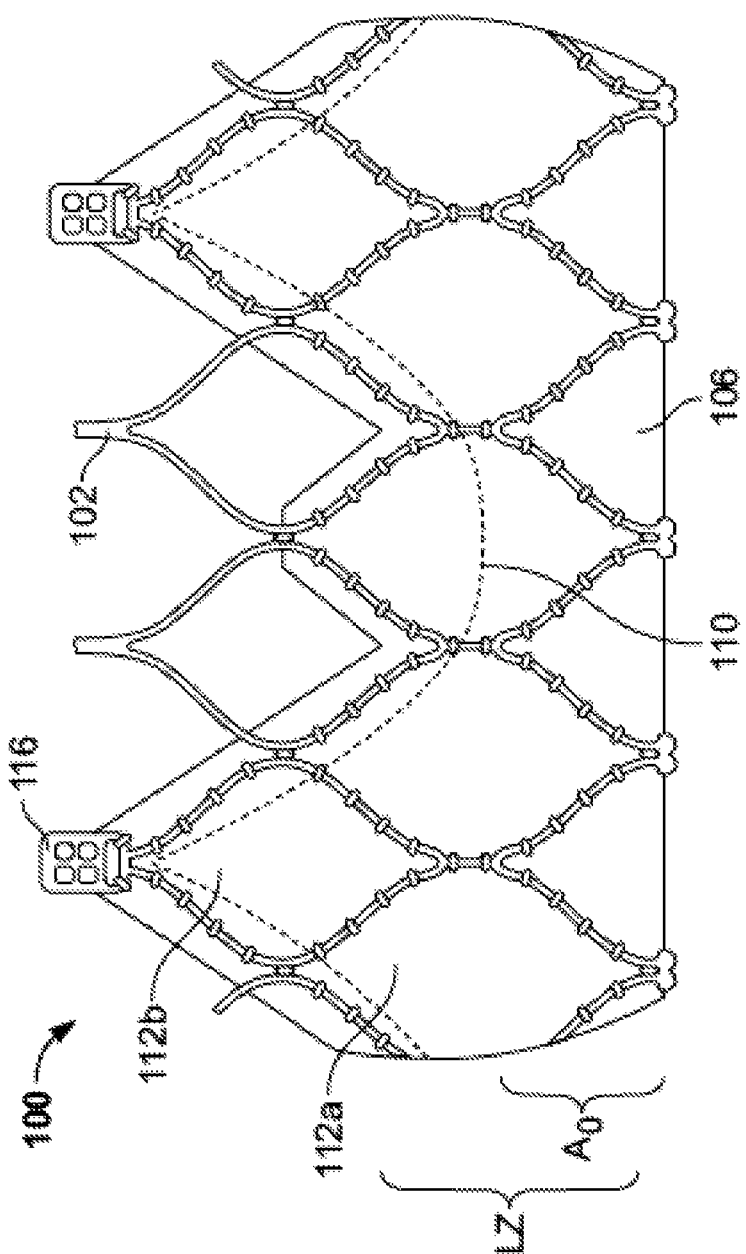
FIG. 1B is a schematic view of the circumference of the prosthetic heart valve of FIG. 1A laid flat out.

The limited space available for such additional features is illustrated more clearly in FIG. 1B, which shows a schematic view of a circumferential portion of valve 100 laid flat out. Leaflet 108 is not illustrated in FIG. 1B, but the point of attachment of leaflet belly 110 is represented by a broken line. If an additional feature, such as a PV leak mitigation feature, were to be attached to cuff 106, it would preferably be positioned in the area $A_O$ between leaflet belly 110 and the proximal or bottom portion of cuff 106. The area $A_O$ between the proximalmost point of stent body 102 and the proximalmost point of attachment of leaflet belly 110 to cuff 106 may be referred to as an area of reduced overlap, because only stent body 102 and cuff 106 overlap in this area. This positioning would be preferable because, as discussed above, it may help minimize the bulk or profile of valve 100, because this positioning would help minimize overlap between cuff 106, leaflet 108, and the additional feature. The area between the proximalmost point of stent body 102 and a proximalmost point in a valley of cuff 106 may be referred to as the landing zone LZ. The landing zone LZ may represent the area of cuff 106 that seals against the anatomy when valve 100 is implanted in a patient. As is described herein, maximizing the proportion of the landing zone LZ which is also an area $A_O$ of reduced overlap may help reduce the profile of valve 100.

Figure 1C:
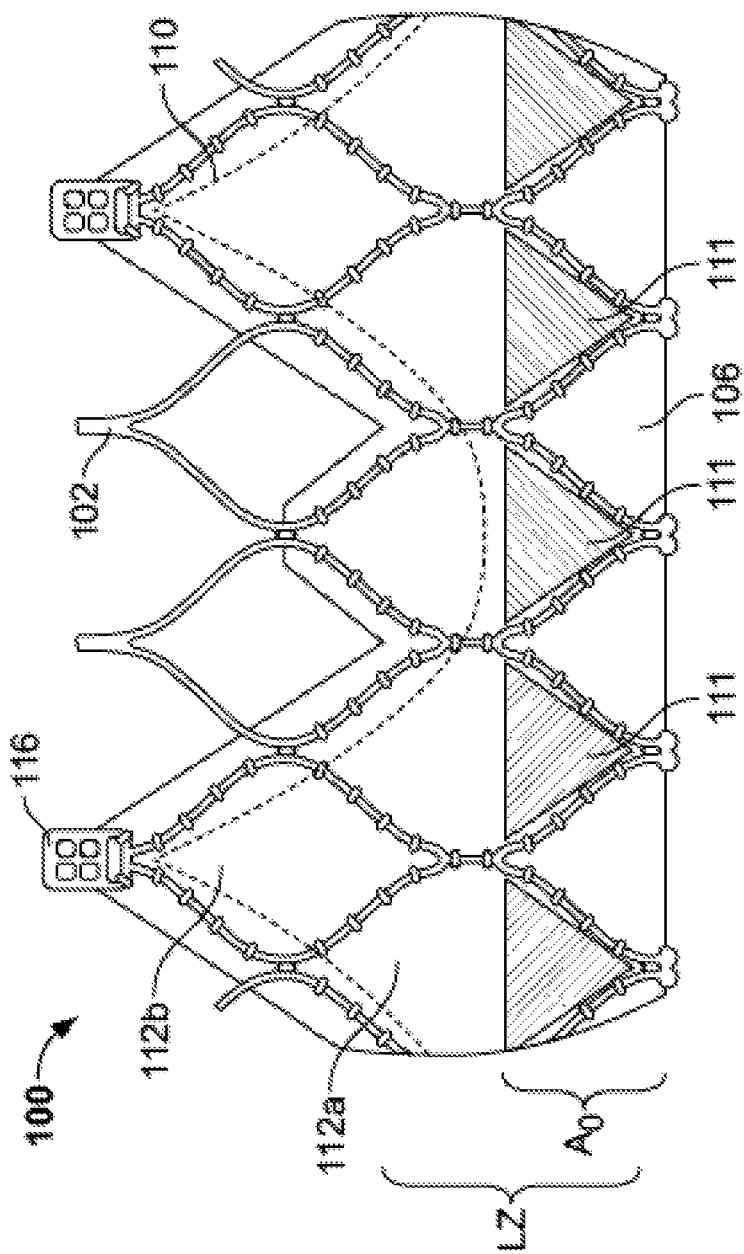
FIG. 1C is a schematic view of the prosthetic heart valve of FIG. 1A laid out with PV leak mitigation features added to the valve.

FIG. 1C illustrates one exemplary additional feature, in particular a PV leak mitigation feature, that could be added on to valve 100. Although valve 100 of FIGS. 1A-B is denoted as a prior art valve, no such representation is made with regards to the addition of the PV leak mitigation feature of FIG. 1C to the prior art valve. This PV leak mitigation feature takes the form of one or more sealing members 111. Sealing members 111 are formed of generally triangular patches that are sewn or otherwise attached to cuff 106 such that a distal or top side of each sealing member remains open but the distal or bottom sides of each sealing member is closed. When valve 100 is implanted, if retrograde blood flow occurs on the abluminal or outer surface of the valve, between the valve and the native annulus in which the valve is implanted, the blood may flow into the open distal side of sealing members 111. The closed proximal sides prevent the blood from exiting sealing members 111. Upon blood flowing into a sealing member 111, it may billow open, like a parachute, resulting in a more complete seal between valve 100 and the patient's anatomy. It should be understood that this is only one type of PV leak mitigation feature that may be added on to valve 100, and other types of features that provide functions other than PV leak mitigation may also be added on to valve 100. Sealing members 111 merely provide one example of an additional feature to provide context for the concepts disclosed herein. It should be noted that, compared to other embodiments described herein, valve 100 with sealing members 111 is relatively bulky because the proportion of the landing zone LZ which has an area $A_O$ of reduced overlap is relatively small.

As is discussed below, by rearranging the relative positions of cuff 106 and leaflet 108 in relation to stent body 102, area $A_O$ may be increased to provide additional space of reduced overlap for adding additional features to valve 100. Also as discussed below, eliminating integral CAF 116 from stent body 102 may also help minimize the bulk and/or profile of valve 100, which may help offset an increase in valve bulk and/or profile resulting from adding additional features to the valve.

Figure 2A:
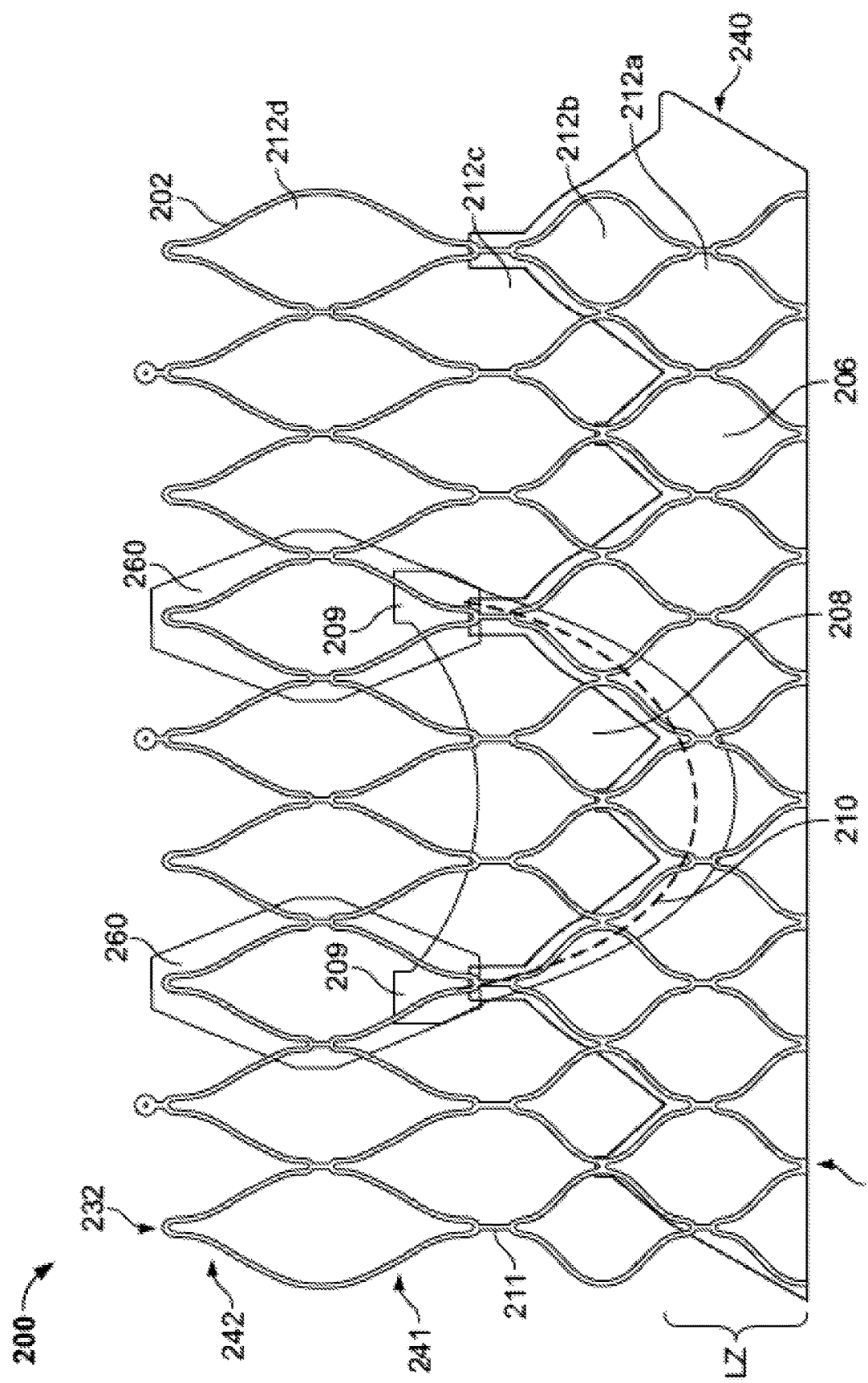
FIG. 2A is a schematic view of the circumference of a prosthetic heart valve laid flat out, according to an embodiment of the disclosure.

FIG. 2A shows a prosthetic heart valve 200 according to an embodiment of the disclosure, with the valve illustrated as a flat representation of the circumference of the valve with only one of three leaflets shown. Prosthetic heart valve 200 includes expandable stent 202, which may be similar or identical to stent 102 of FIG. 1A. Stent 202 extends from proximal or annulus end 230 to a distal or aortic end 232, and includes tubular annulus section 240 adjacent the proximal end and aortic section 242 adjacent the distal end. Transition section 241 may connect annulus section 240 to aortic section 242. Each of the sections of stent 202 includes a plurality of cells connected to one another in one or more annular rows around the stent. For example, as shown in FIG. 2A, annulus section 240 may define a first proximal-most annular row of annulus cells 212a and a second relatively distal annular row of annulus cells 212b. A third row of intermediate cells 212c distal to both rows of annulus cells 212a, 212b may be located between annulus section 240 and aortic section 242. Aortic section 242 may have a fourth distalmost row of aortic cells 212d. Stent body 202 may also include a number of strut intersections 211, that is, portions of the stent body where adjacent cells, such as intermediate cells 212c, meet or intersect. It should be understood that more or fewer rows of cells may be included in stent 202.

Prosthetic heart valve 200 includes a valve assembly secured to stent 202. The valve assembly includes cuff 206 and a plurality of leaflets 208 having attachment tabs 209 (only one leaflet illustrated in FIG. 2A). It should be appreciated that other prosthetic heart valves with which the present disclosure may be used may have more or fewer leaflets.

Figure 2B:
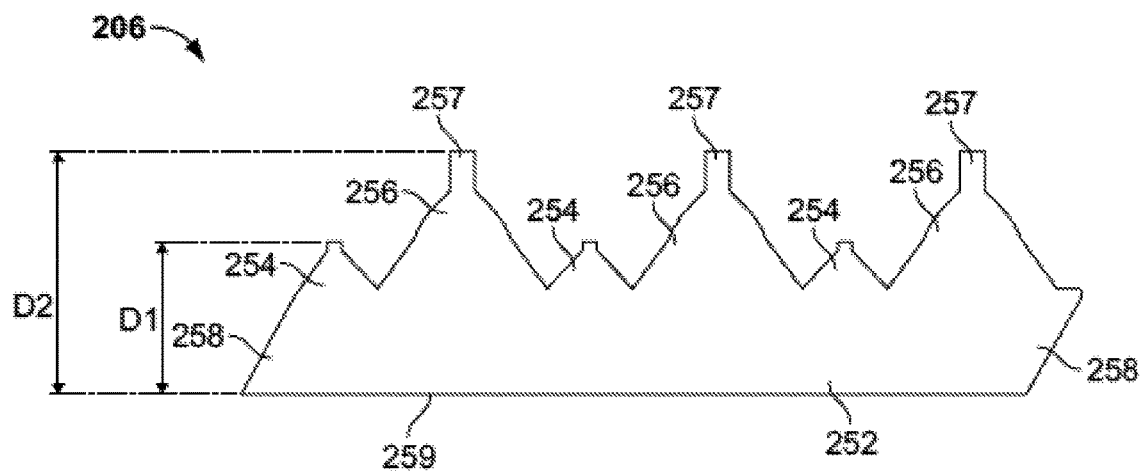
FIG. 2B is a front plan view of the cuff of FIG. 2A.

Cuff 206, which is also illustrated in FIG. 2B, includes a body 252, a series of first posts 254, a series of second posts 256, and a pair of attachment portions 258. The series of first posts 254 include a number of spaced apart extensions that are generally triangular. The series of second posts 256 also include a number of spaced apart extensions that are generally triangular. Second posts 256 may include tabs 257 at distal ends thereof to facilitate attachment to strut intersections 211. Various suture patterns, such as one similar to that shown in FIG. 1B, may be used to attach first posts 254, second posts 256, and the remaining portions of cuff 206 to stent body 202. Although cuff 206 may be formed of a single piece of material, other configurations are possible, such as multiple sections attached together, including, for example, a triple composite cuff formed of three sections stitched or otherwise connected together.

First posts 254 extend a first distance $D_1$ distally from a base 259 of cuff 206. Second posts 256 extend a second distance $D_2$ distally from the base 259 of cuff 206, the second distance being greater than first distance $D_1$. This is true whether or not tab 257 is included in distance $D_2$. Generally, the distances $D_1$ and $D_2$ are preferably minimized such that cuff 206 comprises a relatively small amount of material. Less material generally translates to less bulk and/or a small valve profile. However, cuff 206 preferably includes enough material to provide a support to which leaflet 208 may be attached. Cuff 206 may include valleys between adjacent posts 254, 256, such that a distal portion of the cuff forms general "V" or "W" shapes. As seen in FIG. 2A, leaflet belly 210 is stitched along the dashed line to cuff 206. The shape of cuff 206 helps to minimize the volume of cuff 206 while still providing support for attachment of leaflet 108.

Attachment portions 258 of cuff 206 may overlap one another and may be coupled together using a suture, an adhesive or any other suitable means. Cuff 206 may be placed in the wrapped configuration either before, during, or after being coupled to a stent 202. It should be noted that alternate mechanisms may be used to put cuff 206 into the wrapped configuration.

Referring again to FIG. 2A, stent 202 does not include traditional CAFs as illustrated in FIG. 1A. In other words, stent 202 does not include CAFs that are integral with, unitary with, or otherwise defined by, the stent. As discussed above, the lack of a traditional CAF may decrease the profile of valve 200 and may also improve the tracking ability of the valve. This decrease in bulk and/or profile may help compensate for an increase in bulk if other additional features are attached to valve 200. Because of the lack of a traditional CAF, another method must be used to attach leaflet 208 to valve 200.

Figure 2C:
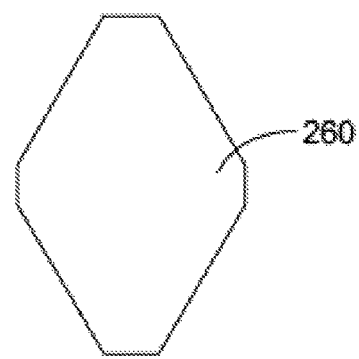
FIG. 2C is a front plan view of an attachment panel of FIG. 2A.

In this particular embodiment, instead of being attached to traditional CAF, leaflet 208 is attached to leaflet attachment panels 260, which are independent of the leaflet, for example by suturing tabs 209 of the leaflet to the leaflet attachment panels. As is described in greater detail below, leaflet attachment panels 260 may facilitate attaching leaflets 208 to stent 202 at positions that provide more space to attach additional features to the valve while reducing overlap between the stent, leaflets, cuff, and additional features. An exemplary panel 260 is also illustrated in FIG. 2C. Panel 260 is generally diamond-shaped and configured to span at least a portion of a cell, in particular a distalmost aortic cell 212d of stent 202. Panel 260 may be formed of a fabric, such as uncalendered polyethylene terephthalate (PET) (200 picks by 200 ends, serial number 4767) produced by Secant Medical of Perkasie, Pa. However, other materials, fiber sizes, and weave patterns may be used to form panel 260. For example, panel 260 could be formed of dry tissue (e.g. glycerol impregnated or freeze dried), tissue with support structures, wire mesh, radiopaque wire, fabrics including polytetrafluoroethylene (PTFE) and ultra high molecular weight polyethylene (UHMWPE) (with or without gel coating), multi-layered composites of any of these materials, and combinations thereof. Panels 260 may be attached to distalmost aortic cells 212d at spaced locations around the circumference of stent 202, for example by sutures attaching the panels to struts of the stent, or any other suitable attachment means. For a tri-leaflet valve, three panels 260 in a spaced apart circumferential relationship may be attached to stent 202 to facilitate attachment of three leaflets 208 to the stent. However, more or fewer panels 260 may be appropriate for valves with more or fewer leaflets 208. For example, two panels 260 may be appropriate for a prosthetic bicuspid valve to replace, for example, a mitral valve.

Panel 260 facilitates attachment of leaflet 208 to stent 202 at any point on the panel using similar methods when using a traditional CAF, but eliminating the need for a traditional CAF. Traditional CAFs are generally formed at the intersection of four cells (see FIG. 1A), limiting the points of attachment available for leaflets. This limitation is not present when using panels 260. For example, leaflet 208 may be sewn to panel 260 at a proximal portion of the panel (as illustrated in FIG. 2A), but may also be attached to a center, medial, lateral, or distal portion of panel 260. Although stent 202 preferably does not include any traditional CAFs, panels 260 may still be advantageously used on a stent with CAFs. This case may arise, for example, if a stent with traditional CAFs is available and desired to be used with panels 260 for convenience without having to create a new stent without traditional CAFs.

As shown in FIG. 2A, each tab 209 of leaflet 208 is attached to a respective panel 260. In this particular embodiment, tabs 209 are sutured to panel 260, but other methods of attachment may be suitable. It should also be noted that panels 260 may be configured with enough material to allow edges of the panels to be wrapped around struts of stent body 202, essentially doubling the thickness of the panels at these wrapped around portions. This may provide for additional strength, if desired. Because there is no need for a traditional CAF, tabs 209 may be attached at locations on panels 260 not previously available. Comparing the position of leaflet 208 of FIG. 2A to the position of leaflet 108 and particularly leaflet belly 110 of FIG. 1B, it can be seen that leaflet 208, including leaflet belly 210 (represented as a broken line) is raised slightly in the distal direction. Raising leaflet 208 distally provides comparatively more space on the landing zone LZ cuff 206 for additional features, such as a PV-leak mitigation feature, with reduced or no overlap between the cuff, leaflet, and additional feature. As is described below in relation to other embodiments, particularly in FIGS. 4A and 5, the relative positions of cuff 206 and leaflet 208 may be changed to a greater extent to provide even more space for attaching additional features. An additional benefit from raising leaflet 208 is that leaflet belly 210 crosses strut intersections 211, which, for example, may provide a useful landmark during assembly.

Figure 3A:
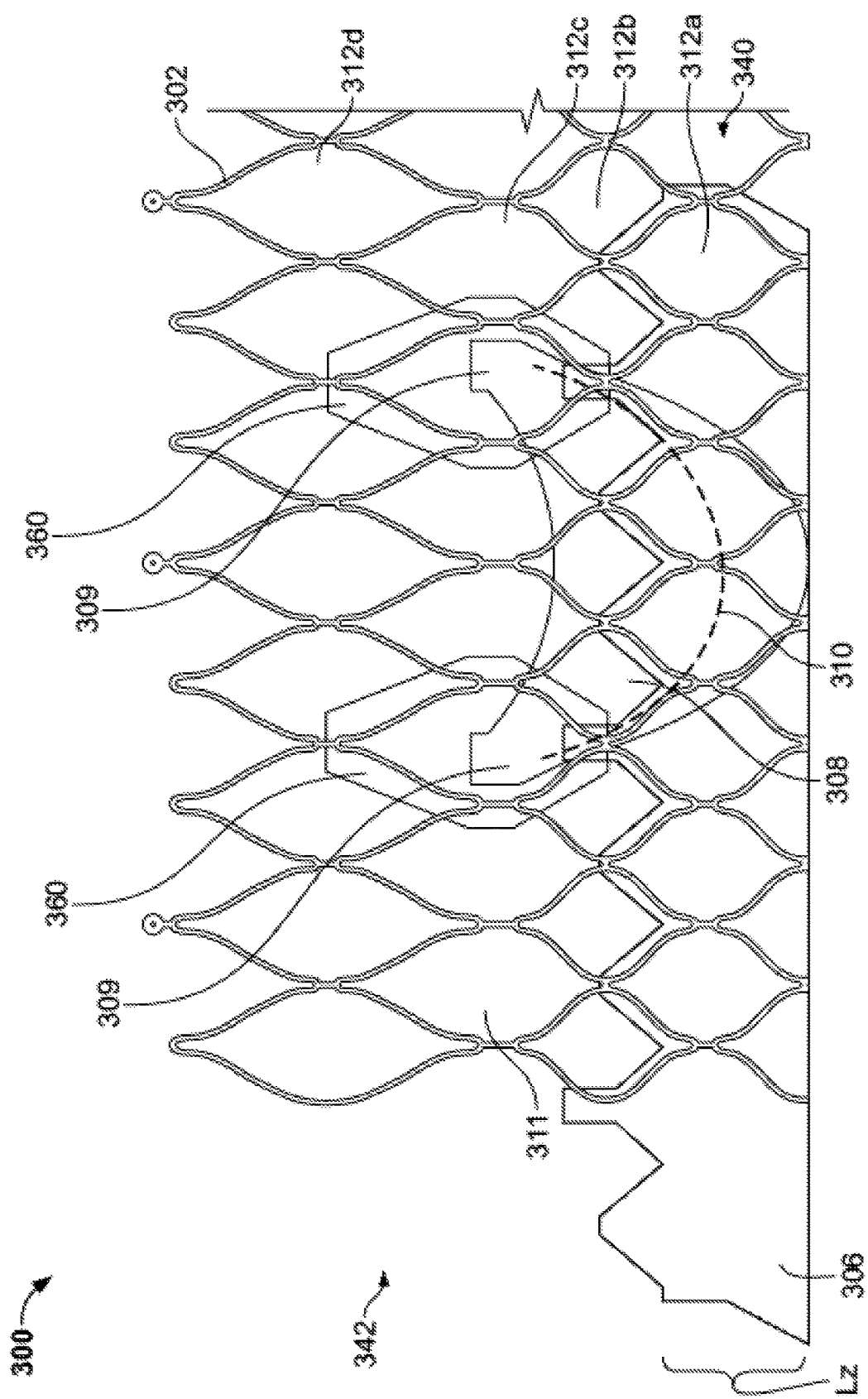
FIG. 3A is a schematic view of the circumference of a prosthetic heart valve laid flat out, according to an alternate embodiment of the disclosure.

FIG. 3A shows a prosthetic heart valve 300 according to an embodiment of the disclosure, with the valve illustrated as a flat representation of the circumference of the valve with only one of three leaflets shown. Prosthetic heart valve 300 includes expandable stent 302, which may be similar or identical to stents 202 of FIG. 2A. For example, stent 302 may have a first proximalmost annular row of annulus cells 312a and a second relatively distal annular row of annulus cells 312b. A third row of intermediate cells 312c distal to both rows of annulus cells 312a, 312b may be located between an annulus section 340 and aortic section 342 of stent 302. The aortic section may have a fourth distalmost row of aortic cells 312d.

Prosthetic heart valve 300 includes a valve assembly secured to stent 302. The valve assembly includes cuff 306 and a plurality of leaflets 308 (only one leaflet illustrated in FIG. 3A). It should be appreciated that other prosthetic heart valves with which the present disclosure may be used may have more or fewer leaflets.

Figure 3B:
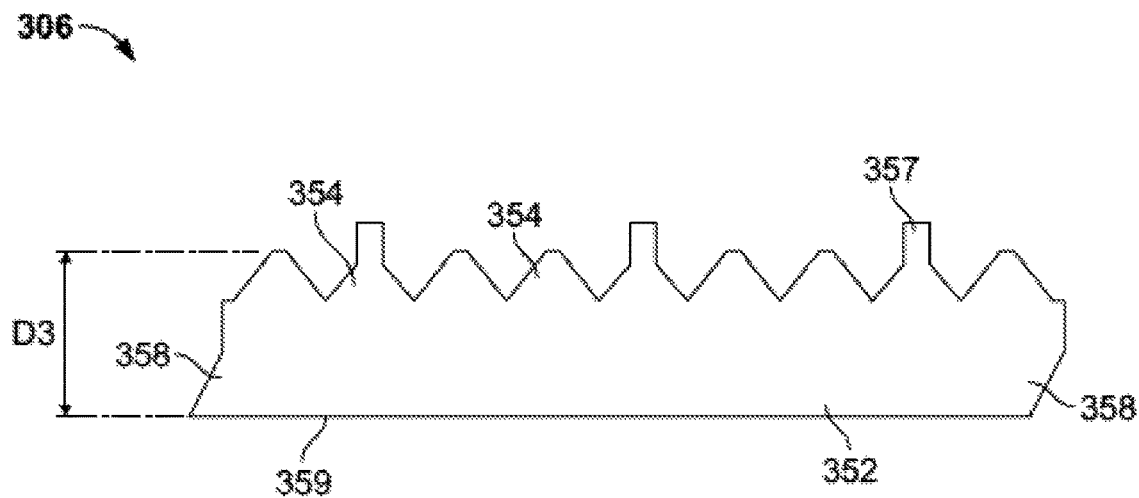
FIG. 3B is a front plan view of the cuff of FIG. 3A

Cuff 306, which is also illustrated in FIG. 3B, includes a body 352, a series of posts 354 and a pair of attachment portions 358. Each post 354 may be generally triangular and similar in configuration, although some of the posts may include tabs 357 at distal ends thereof to facilitate attachment to strut intersections 311. Each group of two adjacent posts 354 configured to correspond to the placement of leaflet belly 310 (i.e. posts that do not have tabs 357) may alternately take other shapes to further reduce the amount of material overlap. For example, posts 354 not having tabs 357 may be generally straight or "U"-shaped. In the particular embodiment shown, three posts 354 include tabs 357, which may be particularly suited for use with a tri-leaflet valve. Each post 354 with a tab 357 is surrounded by two posts without a tab on each side. This particular configuration of posts 354 may be adjusted for different stent configurations, for example with more or fewer posts 354 for stents with more or fewer cells, and with more or fewer tabs 357 for valves with more or fewer leaflets. Each post 354 extends the same or nearly the same distance $D_3$ distally from a base 359 of cuff 306, not including tabs 357. Posts 354 with tabs 357 may extend a slightly greater distance distally from the base 359 of cuff 306 than the posts without the tabs. Comparing valve 200 to valve 300, leaflets 308 are positioned lower or more proximally than leaflets 208. This, in turn, allows for posts 354 of cuff 306 to extend a short distance D3 distally compared to posts 256 of cuff 206. As described above, this shorter distance results in cuff 306 having less volume of material, and thus reducing the bulk of valve 300. However, there is still enough material on cuff 306 to provide for attachment of leaflet 308 because the leaflet is placed lower or more proximally on stent body 302 compared to leaflet 208 on stent body 202 (compare FIG. 2A to FIG. 3A).

Attachment portions 358 may overlap one another and may be coupled together using a suture, an adhesive or any other suitable means. Cuff 306 may be placed in the wrapped configuration either before, during, or after being coupled to a stent 302.

Figure 3C:
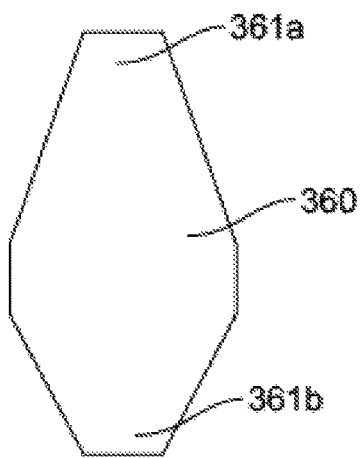
FIG. 3C is a front plan view of an attachment panel of FIG. 3A.

Referring again to FIG. 3A, as with stent 202 of FIG. 2A, stent 302 does not include traditional CAFs, such as those illustrated in FIG. 1A. As described above, the elimination of integral CAFs may help to reduce the bulk and/or profile of valve 300 and improve its tracking ability. In this particular embodiment, instead of being attached to a traditional CAF, leaflet 308 is attached to panels 360, one of which is illustrated in FIG. 3C. Panel 360 is generally diamond-shaped, like panel 260, but has a distal end 361a that is elongated relative to a proximal end 361b. This shape facilitates attachment to a cell, in particular an intermediate cell 312c of stent 302. Panels 360 may be attached to intermediate cells 312c at spaced locations around the circumference of stent 302, for example by sutures attaching the panels to struts of the stent, or any other suitable attachment means. For a tri-leaflet valve, three panels 360 may be attached to stent 302 to facilitate attachment of three leaflets 308 to the stent. However, more or fewer panels 360 may be appropriate for valves with more or fewer leaflets 308.

Panels 360 provide a similar function as panels 260, that is, they facilitate attachment of leaflets 308 to stent 302 at any point on the panel, eliminating the need for a traditional CAF. As shown in FIG. 3A, each tab 309 of leaflet 308 is attached to a respective panel 360, in this case near a point toward the center of intermediate cells 312c. Comparing the position of leaflet 308 of FIG. 3A to the position of leaflet 108 of FIG. 1B, it can be seen that leaflet 308, including leaflet belly 310 (represented as a broken line) is generally at the same position. However, cuff 306, compared to cuff 106 of FIG. 1, despite having a similar landing zone LZ, is relatively small, particularly in the distance from the base to the end of any given post. This results in reduced overlap between cuff 306 and leaflet 308 compared to cuff 106 and leaflet 108, and a corresponding reduction in profile of valve 300 compared to valve 100. By reducing the profile, as discussed above, additional components, such as PV-leak mitigation features, may be added to valve 300, such that the profile of valve 300 with additional features is a similar size as the profile of valve 100 without the additional features.

Figure 4A:
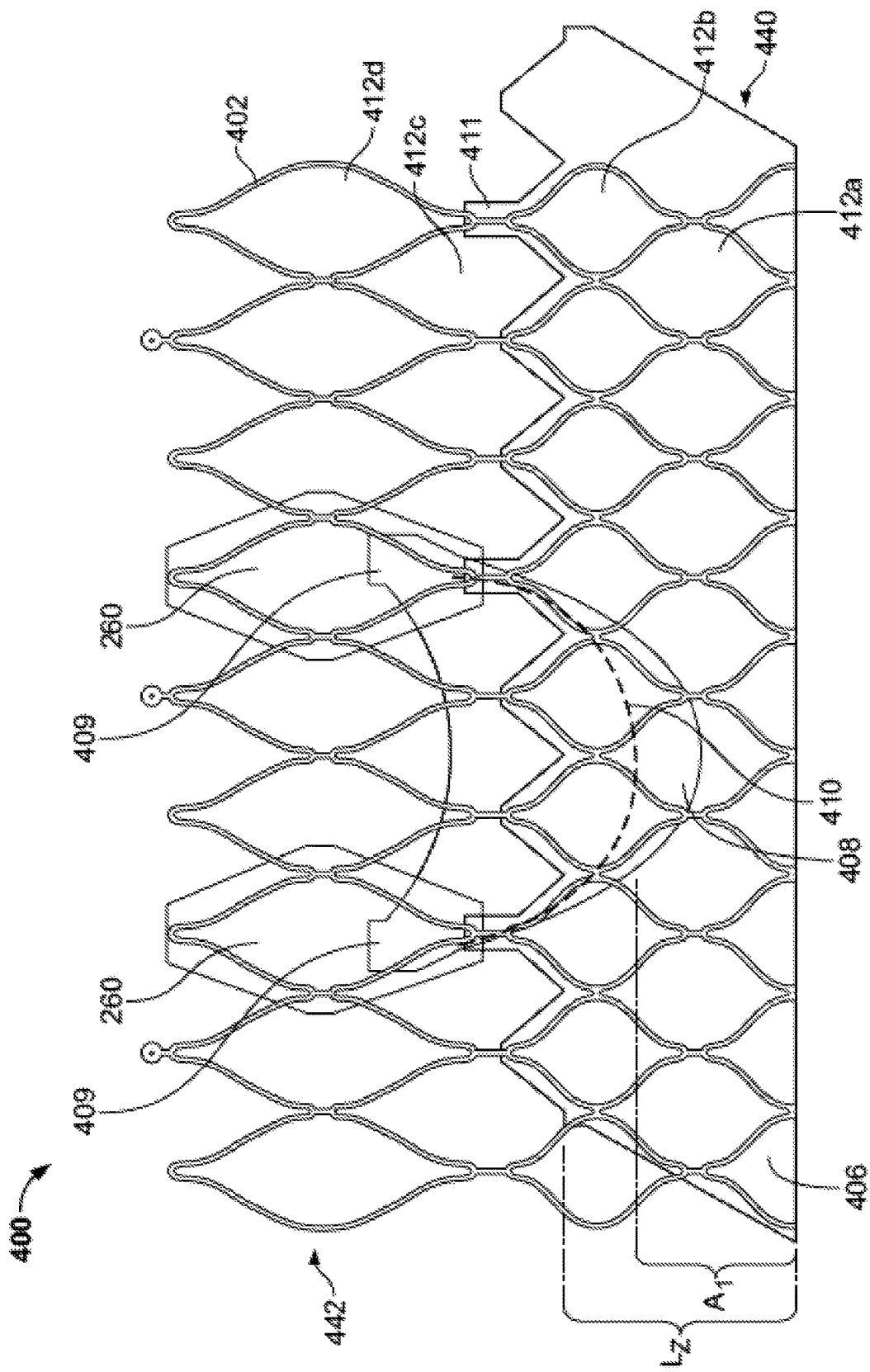
FIG. 4A is a schematic view of the circumference of a prosthetic heart valve laid flat out, according to another embodiment of the disclosure.

FIG. 4A shows a prosthetic heart valve 400 according to an embodiment of the disclosure, with the valve illustrated as a flat representation of the circumference of the valve with only one of three leaflets shown. Prosthetic heart valve 400 includes expandable stent 402, which may be similar or identical to stents 202, 302 of FIGS. 2A, 3A. For example, stent 402 may have a first proximalmost annular row of annulus cells 412a and a second relatively distal annular row of annulus cells 412b. A third row of intermediate cells 412c distal to both rows of annulus cells 412a, 412b may be located between an annulus section 440 and aortic section 442 of stent 402. The aortic section may have a fourth distalmost row of aortic cells 412d.

Prosthetic heart valve 400 includes a valve assembly secured to stent 402. The valve assembly includes cuff 406 and a plurality of leaflets 408 (only one leaflet illustrated in FIG. 4A). It should be appreciated that other prosthetic heart valves with which the present disclosure may be used may have more or fewer leaflets.

Cuff 406, which is also illustrated in FIG. 4B, includes a body 452, a series of posts 454 and a pair of attachment portions 458. Each post 454 may be generally triangular and similar in configuration, although some of the posts may include tabs 457 at distal ends thereof to facilitate attachment to strut intersections 411. Each group of two adjacent posts 454 configured to correspond to the placement of leaflet belly 410 (i.e. posts that do not have tabs 457) may alternately take other shapes to further reduce the amount of material overlap. For example, posts 354 not having tabs 457 may be generally straight or "U"-shaped. In the particular embodiment shown, three posts 454 include tabs 457, which may be particularly suited for use with a tri-leaflet valve. Each post 454 with a tab 457 is surrounded by two posts without a tab on each side. Each post 454 extends the same or nearly the same distance $D_4$ distally from a base 459 of cuff 406, not including tabs 457. Posts 454 with tabs 457 may extend a slightly greater distance distally from the base of cuff 406 than the posts without the tabs. Compared to cuff 306 of FIG. 3B, cuff 406 is a "taller" or "higher" cuff, as distance $D_4$ of cuff 406 is greater than distance $D_3$ of cuff 306. This results in a larger landing zone LZ, as shown in FIG. 4A. This configuration may be particularly suited for valve 400 because leaflet 409 is attached to stent body 402 higher or more distally than other embodiments described above. Although the taller cuff 406 may result in more cuff material compared to, for example, cuff 306, it may be necessary to provide enough material for attachment of leaflet 409, for example by stitching along leaflet belly 410, to the cuff.

Attachment portions 458 may overlap one another and may be coupled together using a suture, an adhesive or any other suitable means. Cuff 406 may be placed in the wrapped configuration either before, during, or after being coupled to a stent 402.

Referring again to FIG. 4A, as with stent 202 of FIG. 2A and stent 302 of FIG. 3A, stent 402 does not include traditional CAFs, such as those illustrated in FIG. 1. As described above, the elimination of integral CAFs may help to reduce the bulk and/or profile of valve 400 and improve its tracking ability. In this particular embodiment, instead of being attached to a traditional CAF, leaflet 408 is attached to panels 260, such as that illustrated in FIG. 2C.

Panels 260 provide the same function for valve 400 as they do for valve 200. As shown in FIG. 4A, each tab 409 of leaflet 408 is attached to a respective panel 260, in this case near a point toward a proximal end of aortic cells 412d. Comparing the position of leaflet 408 of FIG. 4A to the position of leaflet 108 of FIG. 1B, it can be seen that leaflet 408, including leaflet belly 410 (represented as a broken line) is positioned far more distally in relation to the stent. This results in a larger area $A_1$ of reduced or no overlap between cuff 406 and leaflet 408 in landing zone LZ compared to cuff 106 and leaflet 108. In addition to a reduction in profile of valve 400 compared to valve 100, the larger area $A_1$ provides space for the addition of extra features, such as PV-leak mitigation features. The area $A_1$ of reduced overlap may also be thought of as having a longitudinal length, that is, a length between the proximalmost end of stent body 402 and the proximalmost point of attachment of leaflet belly 410 to cuff 406. The longitudinal length may be measured along a line that is generally parallel to a longitudinal axis of valve 400.

Figure 5:
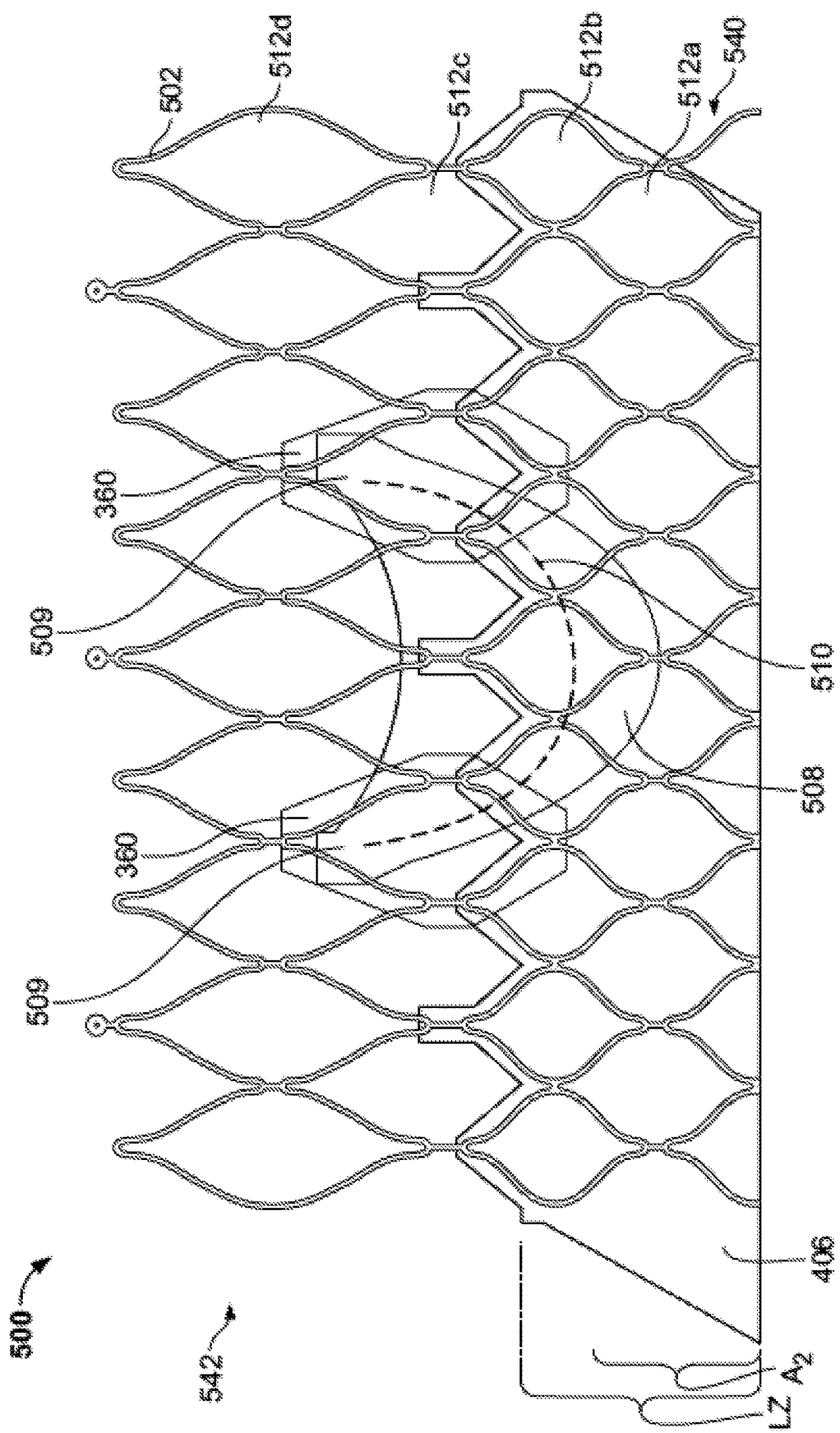
FIG. 5 is a schematic view of the circumference of a prosthetic heart valve laid flat out, according to another embodiment of the disclosure.

FIG. 5 shows a prosthetic heart valve 500 according to an embodiment of the disclosure, with the valve illustrated as a flat representation of the circumference of the valve with only one of three leaflets shown. Prosthetic heart valve 500 includes expandable stent 502, which may be similar or identical to stents 202, 302 and 402 of FIGS. 2A, 3A, and 4A. For example, stent 502 may have a first proximalmost annular row of annulus cells 512a and a second relatively distal annular row of annulus cells 512b. A third row of intermediate cells 512c distal to both rows of annulus cells 512a, 512b may be located between an annulus section 540 and aortic section 542 of stent 502. The aortic section may have a fourth distalmost row of aortic cells 512d. Prosthetic heart valve 500 includes a valve assembly secured to stent 502. The valve assembly includes cuff 406, which is the same "high" cuff shown in FIG. 4B with a large landing zone LZ and a plurality of leaflets 508 (only one leaflet illustrated in FIG. 5). It should be appreciated that other prosthetic heart valves with which the present disclosure may be used may have more or fewer leaflets.

Valve 500 is identical to valve 400 in most respects, with the exception that leaflet 508 is attached to panels 360 (illustrated in FIG. 3C). Panels 360 are attached to cells in intermediate row of cells 512c, and tabs 509 of leaflet 508 are attached to the panels at a distal portion thereof. Comparing the position of leaflet 508 of FIG. 5 to the position of leaflet 108 of FIG. 1B, again it can be seen that leaflet 508, including leaflet belly 510 (represented as a broken line) is positioned more distally in relation to the stent. This results in a larger area $A_2$ in the landing zone LZ of reduced or no overlap between cuff 406 and leaflet 508 compared to cuff 106 and leaflet 108. In addition to a reduction in profile of valve 500 compared to valve 100, the larger area $A_2$ provides space for the addition of extra features, such as PV-leak mitigation features. This smaller profile and larger area $A_2$ is similar to the result of the configuration of valve 400 of FIG. 4A, even though the leaflets 408 and 508 are attached to the respective stents 402, 502 at different levels. That is, despite the fact that leaflet 408 is attached to stent 402 at aortic cells 412d and that leaflet 508 is attached to stent 502 at intermediate cells 512c, the respective panels provide the ability to attach the leaflets to the cells at different locations within the cells, resulting in similar profiles and reduced areas of overlap. In addition to providing the ability of raising leaflet belly 510, this configuration provides the ability of leaflets 508 to be attached anywhere along the height of panels 360. The height of panel 360 and point of attachment of leaflets 508 may both help to facilitate positioning the prosthetic valve above areas of the native valve that may distort the function of the prosthetic valves.

As should be clear from the description of the foregoing embodiments, the size of the area of reduced overlap in the landing zone, defined as the area between the proximal end of the stent body and the proximalmost point of attachment of the leaflet belly to the cuff, depends on at least two factors. First, the circumferential row to which the particular panel is attached affects the size of the area of reduced overlap. Second, the position at which the leaflet is attached to the panel affects the size of the area of reduced overlap. All else being equal, the area of reduced overlap increases in size when the panel is attached to a more distal row of cells. Similarly, all else being equal, the area of reduced overlap increases in size when the leaflet is attached to a more distal position on the panel.

If using leaflet attachment panels, such as panels 260 or 360, different valve characteristics may be imparted by attaching the panels to intermediate cells (e.g. 512c) compared to aortic cells (e.g. 512d). The differences may be seen by comparing FIGS. 2A, 3A, 4A, and 5. However, the valves 200, 300, 400 and 500 in FIGS. 2A, 3A, 4A and 5 are illustrated as flat representations. In a three-dimensional expanded configuration, such as that shown in FIG. 1A, the aortic section of a valve generally flares outwardly. Attaching panels (and thus leaflets) to a flared portion of a stent may result in different forces being applied to the leaflet and/or the stent body, and different leaflet motion or constriction, particularly when the valve is in the expanded configuration. For example, attaching leaflets to panels at a flared portion of the stent body may lead to a high and tight configuration, which may restrict leaflet motion and reduce abrasion on the stent, but the different forces may positively (or negatively) affect valve durability.

As should be apparent from the description of valves 200, 300, 400, and 500 above, profile reduction and redistribution of the cuff and leaflet may be accomplished by using cuffs of different designs and by attaching leaflets to the stent at points distal to the location of traditional CAFs. This has the added benefit of permitting traditional CAFs to be eliminated from the design, which may further reduce the valve profile and improve tracking ability. Although two examples of panels 260, 360 were illustrated in the different valves described above, a number of alternate panels may be suitable for use with the disclosure, and the panels may even be eliminated altogether.

Figure 6B:
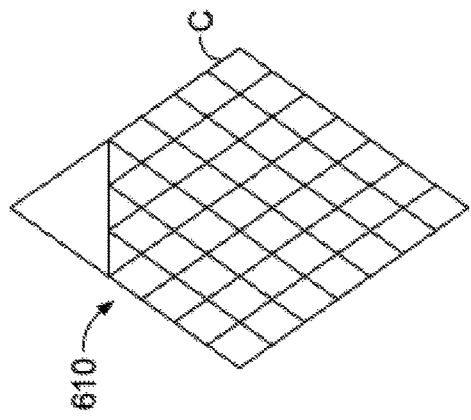
FIGS. 6A-F are schematic views of different attachment panels attached to a cell of a stent body according to the disclosure showing the weave patterns of the panels, with the remaining portions of the stent body omitted.
Figure 6D:
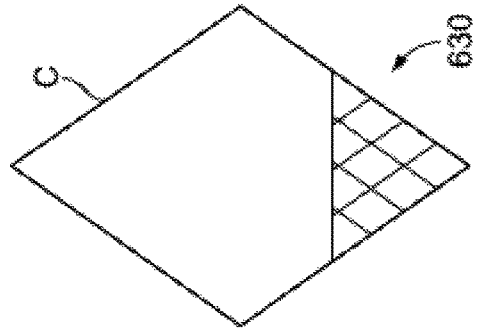
Figure 6A:
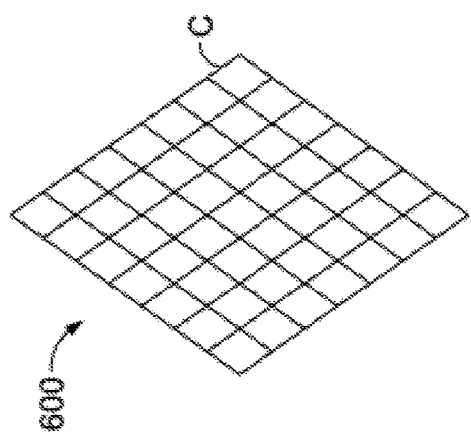

For example, FIGS. 6A-F show a variety of configurations of panels to facilitate leaflet attachment to cells of a stent. FIG. 6A shows a panel 600 spanning the entire area of a cell C of a stent body, with the remainder of the stent body omitted from the figure. Both panels 260, 360 of the above described valves take this form, as they both span entire cells. When panel 600 is formed of a fiber, the weave of the fiber may be oriented generally diagonally across the cell to facilitate leaflet attachment. This generally diagonal orientation may allow the fibers to properly orient when the prosthetic valve changes shape between a collapsed configuration and an expanded configuration. If the fibers were oriented completely longitudinally or circumferentially, undesirable forces could result from the change in shape of the prosthetic valve. It should be noted that the fibers need not be oriented exactly diagonally (i.e. exactly 45 degrees), but may be oriented to allow for the particular panel to collapse and expand with the valve without placing undue forces on the stent body. This generally diagonal orientation may also facilitate the transfer of load from the point of attachments of leaflets to the panel to optimize cushioning of the leaflet tissue when forces are applied to the leaflet, such as those resulting from the valve closing and resisting retrograde flow. The above-described generally diagonal fiber orientation may also reduce the likelihood of deterioration of the fiber panels, such as from tearing or elongation of the fibers or elongation of the attachment suture holes, which can result from, for example, durability cycling of the valve.

Figure 6C:
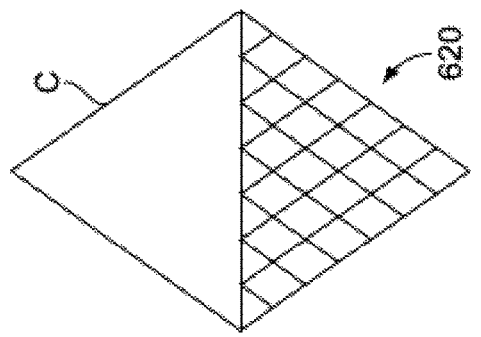
Figure 6F:
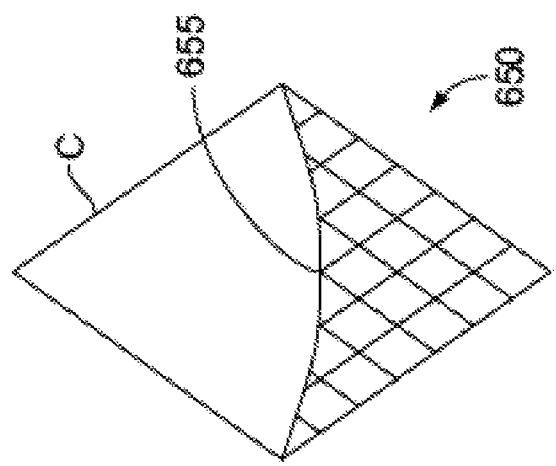
Figure 6E:
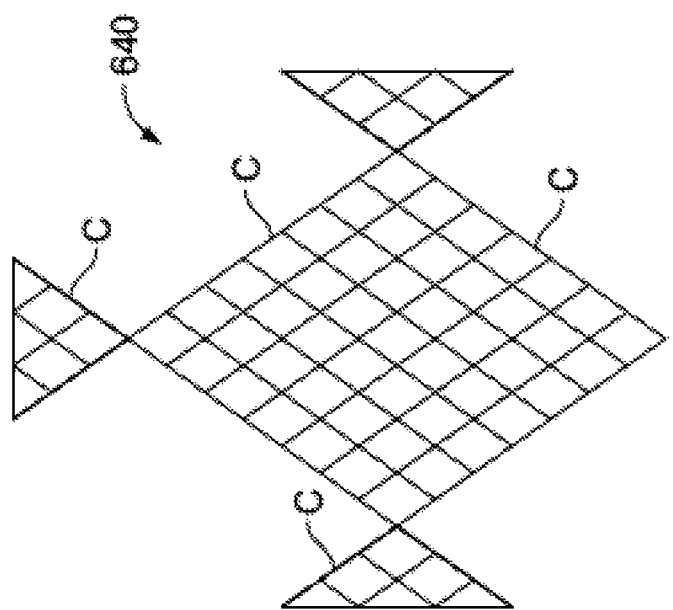

The panel need not span an entire cell C. For example, panel 610, shown in FIG. 6B, spans approximately three-fourths the area of cell C. Using a panel that spans less than an entire cell C may be beneficial in that less material is required. This may reduce the profile of the valve and may generally reduce bulk resulting in enhanced tracking ability. If the leaflet is being attached somewhere in the proximal three-fourths of a cell C, panel 610 may provide ample points for attachment while less material needs to be used in comparison to panel 600. As shown in FIGS. 6C-D, other configurations, including panel 620, which spans approximately half the area of a cell C, and panel 630, which spans approximately one-fourth the area of a cell C, may also be suitable. As with FIG. 6A, the remainder of the stent body is omitted from FIGS. 6B-D. Generally, if less material is used for a given panel, the valve will be less bulky and have a smaller profile. This is counterbalanced in that using too little material may make leaflet attachment difficult, or reduce the stability of the attachment. Although panels that span discrete amounts of a cell C are shown (i.e. full, three-fourths, half, one-fourth), panels that span more or less than these amounts may be used. For example, panel 640 shown in FIG. 6E spans an entire cell C and spans portions of adjacent cells C. The remainder of the stent body is omitted from FIG. 6E. Panel 650, shown in FIG. 6F, occupies slightly less than half of a cell C and includes a curved free edge 655, compared to, for example, the substantially straight free edges in panels 610, 620 and 630. Because leaflets are attached to the panels, and forces are applied to the leaflets during normal operation, forces may tend to pull the panels radially inward toward the center of the stent. The curvature of free edge 655 may provide a different level of support than straight free edges, and, for example, keep the free edge under tension, helping concentrate any applied forces along the curvature. It should be noted that, although panels are generally illustrated as being independent of the cuff, the panels may be part of the cuff, such as forming extensions of the cuff. Any of the panels shown in FIGS. 6A-F can be used with any of the valves disclosed herein, depending on the particular desires of the user. Further, leaflets may be attached to any portion of the panels to provide different leaflet contour and placement options.

FIG. 7 shows a prosthetic heart valve 700 using panel 650 described above, with the valve illustrated as a flat representation of the circumference of the valve with only one of three leaflets shown. Prosthetic heart valve 700 includes expandable stent 702, which may be similar or identical to other stents described herein. Stent 702 may have a first proximalmost annular row of annulus cells 712a and a second relatively distal annular row of annulus cells 712*b*. A third row of intermediate cells 712*c* distal to both rows of annulus cells 712*a*, 712*b* may be located between an annulus section 740 and aortic section 742 of stent 702. The aortic section may have a fourth distalmost row of aortic cells 712*d*. This particular embodiment includes cuff 206, which is the same cuff shown in FIG. 2B, and a plurality of leaflets 708 (only one leaflet illustrated in FIG. 7). It should be appreciated that other prosthetic heart valves with which the present disclosure may be used may have more or fewer leaflets.

Panels 650 are attached to cells in aortic row of cells 712*d*, and tabs 709 of leaflet 708 are attached to the panels at a proximal portion thereof. Compared to, for example valve 200, valve 700 is identical in most respects except that panels 650 are about half the volume of panels 260 of valve 200, and panels 650 include a curved free edge 655 as described above. Valve 700 includes all the benefits described in relation to valve 200, with the additional benefits that panels 650 have less volume than panels 260, and curved free edge 655 may provide additional stability to the attached leaflets 708. As should be apparent, the full panels 260, 360 described in relation to valves 200, 300, 400, and 500 may be replaced by other panels, such as those illustrated in FIGS. 6B-F, depending on the desired effect.

Figure 8A:
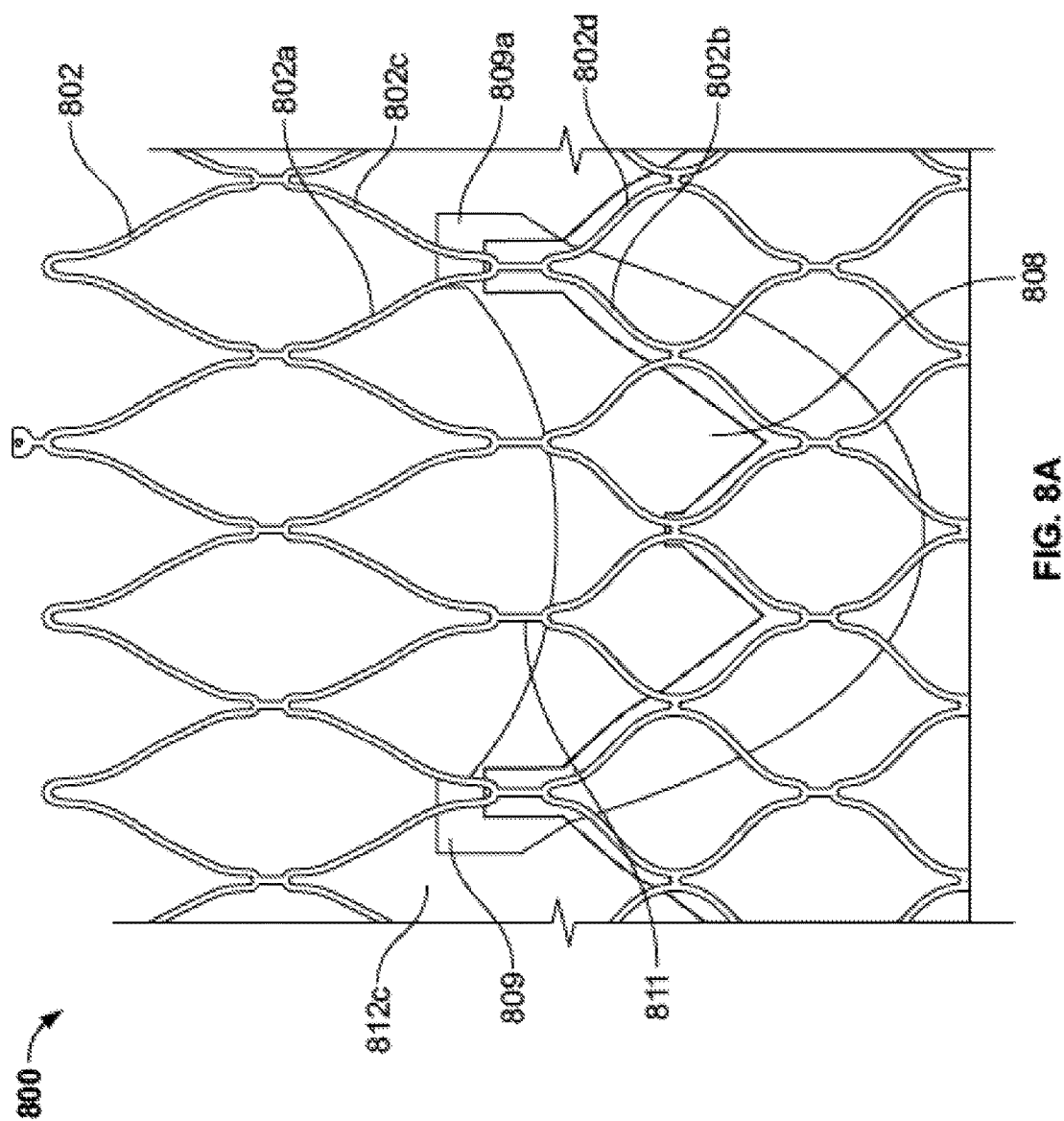
FIG. 8A is a schematic view of the circumference of a prosthetic heart valve laid flat out, according to still yet another embodiment of the disclosure.

In order to even further reduce volume, leaflets may be attached directly to the stent, without using a traditional CAF and eyelets of traditional CAFs, and also without using panels described above. This may slightly limit the options of attaching leaflets at any point on a panel, but the further reduction in volume by elimination of panels may help to further reduce the profile of the stent. For example, FIG. 8A shows a prosthetic heart valve 800 with the valve illustrated as a flat representation of the circumference of the valve with only one of three leaflets shown. Leaflet 808 is attached directly to expandable stent 802 using tabs 809 of the leaflet. The tabs 809 may be attached at any point along struts of stent body 802, including at joints or at non-joint portions. For example, in the illustrated embodiment, tabs of adjacent leaflets (only tab 809*a* of leaflet 808 illustrated for clarity) are each attached to a strut intersection 811 of an intermediate cell 812*c*. In other words, tab 809*a* is attached around a point of stent body 802 where four struts 802*a*, 802*b*, 802*c*, and 802*d* intersect. However, it should be understood that other points of attachment on stent body 802, including non-joint portions, may be suitable.

Figure 8C:
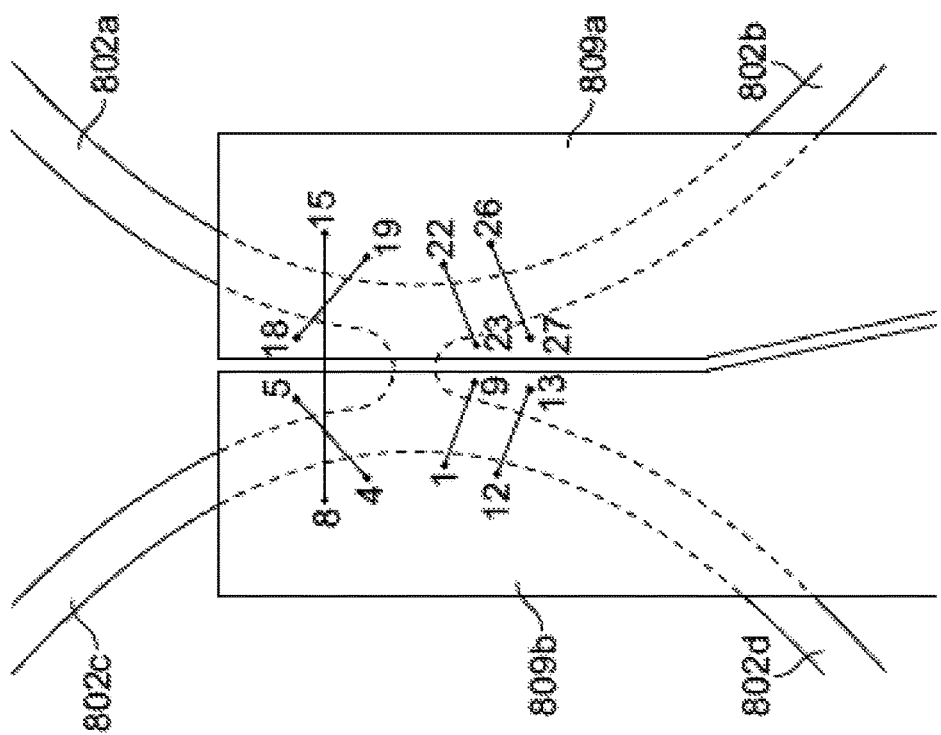
FIG. 8C is a rear view of suture attachments on the luminal side of the prosthetic valve of FIG. 8A.
Figure 8B:
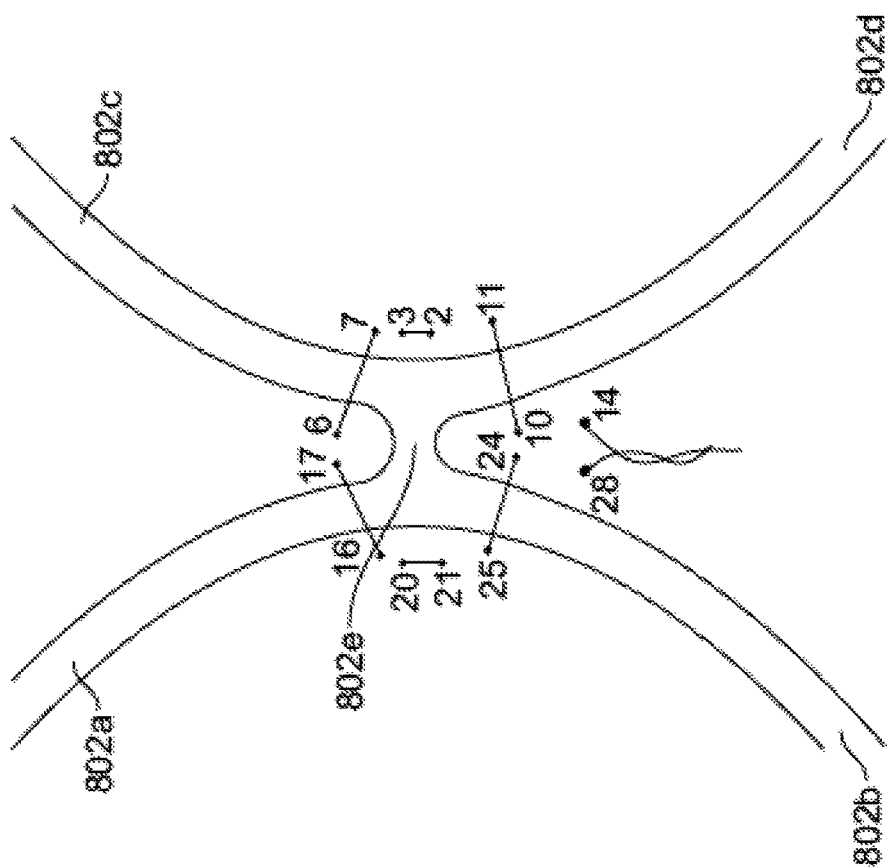
FIG. 8B is a front view of suture attachments on the abluminal side of the prosthetic valve of FIG. 8A.

It should be noted that the embodiments described herein may use the same or similar general leaflet attachment suture patterns and geometries, although variations to such attachment patterns and methods may be suitable for use with the embodiments described herein. FIGS. 8B-C show an exemplary suture pattern that may be used to directly attach leaflets to a stent, with FIG. 8B illustrating a view from the outside of the stent, and FIG. 8C illustrating a view from the inside of the stent. Tabs 809*a*, 809*b* of two different leaflets are illustrated in FIG. 8C, although they are omitted in FIG. 8B for clarity. Also, in FIG. 8C, much of body of stent 802 is illustrated in broken lines behind the leaflets. The following describes the use of a single suture to attach the leaflet tabs 809*a*, 809*b* to stent body 802. It will be understood, however, that multiple sutures may be used for this purpose. For example, one suture may attach first tab 809*a* to stent body 802, while a second, separate suture attaches second tab 809*b* to the stent body.

The suture pattern may begin at any point at or near tabs 809*a*, 809*b* and terminate at any other point. In at least some examples, the suture pattern begins and terminates at the same position. For the sake of illustration, the suture pattern will be described as beginning at point 1. It should be noted that point 1 (FIG. 8C) and point 2 (FIG. 8B) represent the same location on tab 809*a*, but on opposing surfaces of the tab. As used herein, with reference to FIGS. 8B-C, the term "out" indicates passing the suture from the luminal side of the valve through the tab of the leaflet and past the stent structure to the abluminal side of the valve. The term "in" indicates passing the suture from the abluminal side of the valve past the stent structure and through the tab of the leaflet to the luminal side of the valve.

The suture pattern may begin by passing a leading end of a suture out through tab 809*b* point 1. The suture exits tab 809*b* at point 2, is advanced in through point 3 through tab 809*b*, exiting the luminal side at point 4. From point 4, the suture may be crossed over strut 802*c* on a distal side of strut intersection 802*e*, and advanced out of tab 809*b* at point 5, exiting to the luminal side at point 6. The suture may then be crossed over strut 802*c* again, and be advanced into tab 809*b* at point 7, exiting the luminal side at point 8.

At this stage, the trailing end of the suture is on the luminal side of tab 809*b* at point 1. The trailing end of the suture may then cross over strut 802*d* on a proximal side of strut intersection 802*e*, and be advanced out of tab 809*b* at point 9, exiting the abluminal side of tab 809*b* at point 10. The suture may be looped around strut 802*d* again, and then advanced into tab 809*b* at point 11, exiting the luminal side at point 12. The suture may again be wrapped around strut 802*d* once more, and advanced out of tab 809*b* at point 13, exiting the abluminal side of tab 809*b* at point 14. This completes each suture point in tab 809*b*, and the trailing end of the suture may be left undisturbed, exiting the luminal side of tab 809*b* at point 14, until the remainder of the suturing is complete.

The leading end of the suture, at this point exiting the luminal side of tab 809*b* at point 8, may then be wrapped around struts 802*c* and 802*a* on the distal side of strut intersection 802*e*, and then advanced out of tab 809*a* at point 15, coming out the abluminal side at point 16. The suture may then be wrapped around strut 802*a*, and advanced into tab 809*a* at point 17, exiting the luminal side of tab 809*a* at point 18. The suture may be wrapped once more around strut 802*a*, and advanced out of tab 809*a* at point 19, exiting the abluminal side of tab 809*a* at point 20. The suture may be advanced back into tab 809*a* at point 21, exiting the luminal side of tab 809*a* at point 22. The suture may then be wrapped around strut 802*b* on the proximal side of strut intersection 802*e* and advanced out of tab 809*a* at point 23, coming out the abluminal side of tab 809*a* at point 24. The suture may be looped a second time around strut 802*b*, and advanced into tab 809*a* at point 25, coming out the luminal side at point 26. Finally, the suture may be wrapped once more around strut 802*b*, and advanced out of tab 809*a* at point 27, exiting the abluminal side of tab 809*a* at point 28. The leading end of the suture, exiting the abluminal side of tab 809*a* at point 28, and the trailing end of the suture, exiting the abluminal side of tab 809*b* at point 14, may then be knotted or otherwise tied off, completing and securing the suture. As noted above, although described with a particular pattern and the use of a single suture, the use of multiple sutures and/or different suture patterns may be suitable to attach leaflet tabs 809*a*, 809*b* directly to stent body 802.

Figure 9:
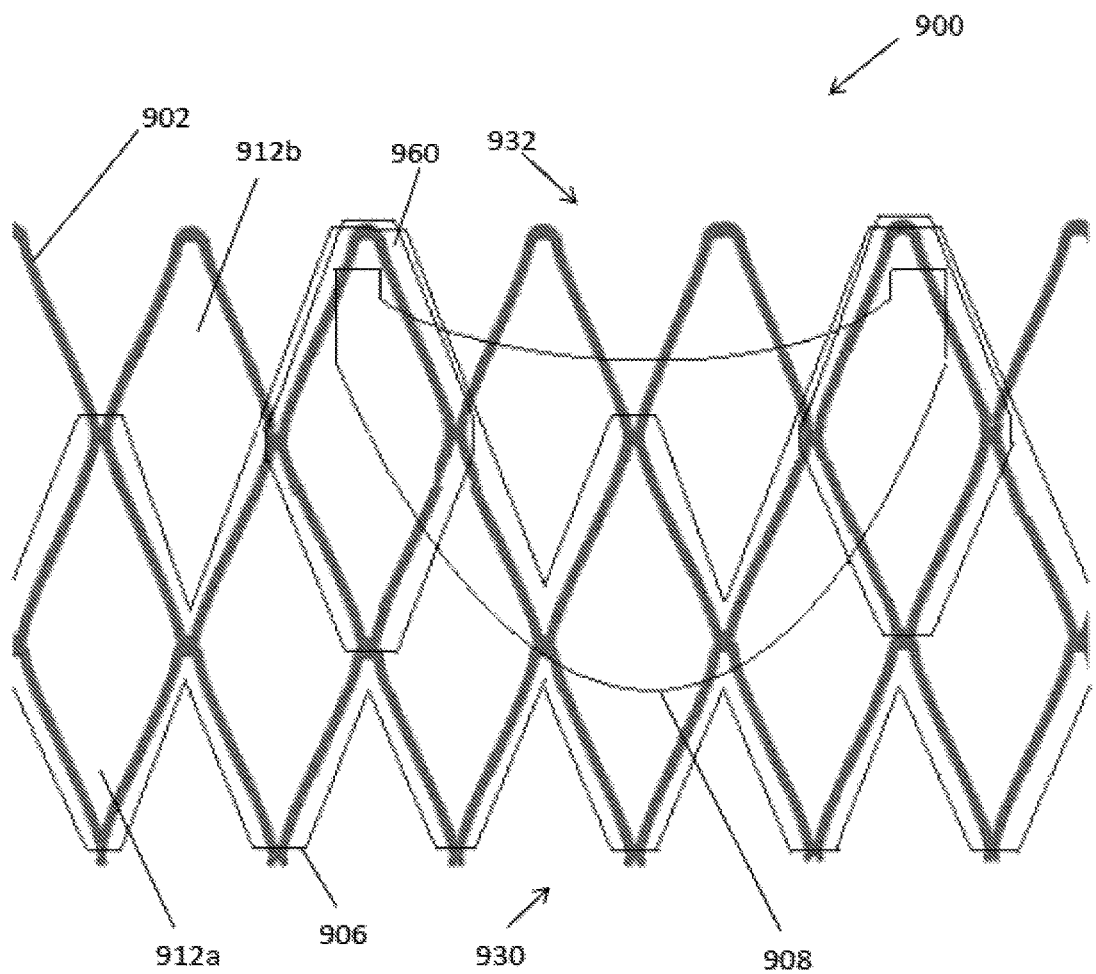
FIG. 9 is a schematic view of a portion of the circumference of a prosthetic mitral valve laid flat out, according to an embodiment of the disclosure.

Although embodiments have generally been described with respect to prosthetic valves for replacement of a native aortic valve, the concepts described herein apply to the replacement of other valves as noted above. For example, FIG. 9 shows a prosthetic heart valve 900 according to an embodiment of the disclosure, intended for replacement of a native mitral valve, with the valve illustrated as a flat representation of a portion the circumference of the valve with only one of two leaflets shown. Prosthetic heart valve 900 includes expandable stent 902, extending from inflow end 930 to an outflow end 932. It should be understood that, when implanted in a native mitral valve annulus, inflow end 930 is closer to the left atrium while outflow end 932 is closer to the left ventricle.

Stent 902 includes a plurality of cells connected to one another in one or more annular rows around the stent. For example, as shown in FIG. 9, stent 902 includes two annular rows of cells, including a first proximal annular row of cells 912a and a second distal annular row of annulus cells 912b. Prosthetic heart valve 900 includes a valve assembly secured to stent 902, including cuff 906 and a plurality of leaflets 908 (only one leaflet illustrated in FIG. 9). When used as a mitral valve replacement, heart valve 900 may include two prosthetic leaflets 908, although more leaflets may be used if desired.

Generally similar to heart valve 200 of FIG. 2A, leaflet 908 of heart valve 900 is attached to stent 902 via leaflet attachment panels 960. Leaflet attachment panel 960 may take a similar or identical form as leaflet attachment panel 260. However, because of the relatively shortened length of stent 902 compared to stent 202, leaflet 908 may be attached to attachment panel 960 closer to outflow end 932. The use of leaflet attachment panel 960 may provide similar benefits as described with respect to other embodiments above. For example, the use of leaflet attachment panel 960 may eliminate the need for traditional CAFs formed of relatively stiff material in the stent 902. This may be of particular benefit for use in prosthetic mitral valves, as CAFs used in prosthetic mitral valves often extend into the left ventricle and may interfere with native structure in the left ventricle or even press on the thin heart wall separating the left ventricle and aortic valve, possible interfering with proper functioning of the aortic valve. Other similar benefits include, for example, the reduction in diameter of heart valve 900 in the collapsed condition and the increased options of points of attachment of leaflet 908 to stent 902.

Figure 10:
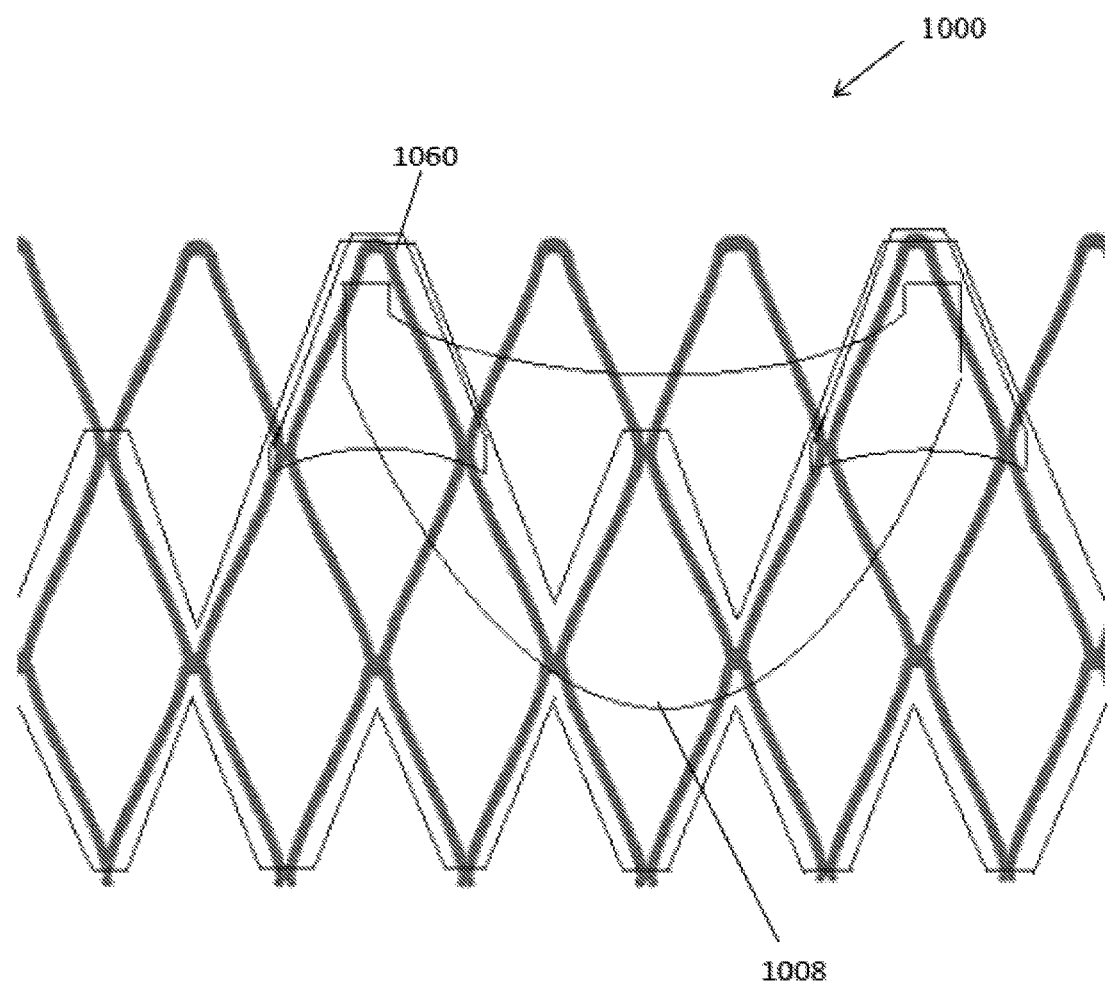
FIG. 10 is a schematic view of a portion of the circumference of a prosthetic mitral valve laid flat out, according to another embodiment of the disclosure.

Just as different types of leaflet attachment panels may be used with prosthetic aortic valves described above, alternative leaflet attachment panels may be used with prosthetic mitral valves. For example, FIG. 10 illustrates prosthetic mitral valve 1000 that is identical to prosthetic mitral valve 900 in all ways other than the leaflet attachment panel. In particular, leaflet 1008 is attached to a leaflet attachment panel 1060 similar leaflet attachment panel 650 of FIG. 6F. Panel 1060, occupies slightly less than half of a stent cell and includes a curved free edge. As noted above, by using a panel that is smaller in size, there is even less bulk to the valve, and traditional CAFs may still not be omitted. It should be understood that heart valve 1000 is just one example of a variation to mitral valve 900 of FIG. 9, and other leaflet attachment panels described herein may be used with a prosthetic mitral valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. It will be appreciated that the various dependent claims and the features set forth therein can be combined in different ways than presented in the initial claims. It will also be appreciated that the features described in connection with individual embodiments may be shared with others of the described embodiments.

The following Paragraphs summarize certain aspects of the disclosure.

Paragraph A: A prosthetic heart valve, comprising: a stent body including a plurality of cells arranged in circumferential rows; a cuff attached to the stent body; at least one leaflet attachment panel attached to and spanning at least a portion of one of the cells; and at least one prosthetic valve element mounted to the at least one leaflet attachment panel; wherein the leaflet attachment panel is not integral with the stent body.

Paragraph B: The prosthetic heart valve of Paragraph A, wherein the prosthetic valve element comprises a leaflet and the leaflet attachment panel is not integral with the leaflet.

Paragraph C: The prosthetic heart valve of Paragraph A, wherein the leaflet attachment panel is integral with the cuff.

Paragraph D: The prosthetic heart valve of Paragraph A, wherein the leaflet attachment panel is not integral with the cuff.

Paragraph E: The prosthetic heart valve of Paragraph A, wherein the leaflet attachment panel is at least partially formed of fabric.

Paragraph F: The prosthetic heart valve of Paragraph A, wherein the leaflet attachment panel is at least partially formed of tissue.

Paragraph G: The prosthetic heart valve of Paragraph A, wherein the leaflet attachment panel spans an area of one entire cell.

Paragraph H: The prosthetic heart valve of Paragraph G, wherein the leaflet attachment panel spans more than the area of one entire cell.

Paragraph I: The prosthetic heart valve of Paragraph A, wherein the leaflet attachment panel spans less than an area of one entire cell, the leaflet attachment panel having a free edge.

Paragraph J: The prosthetic heart valve of Paragraph I, wherein the leaflet attachment panel spans approximately three-fourths the area of one entire cell.

Paragraph K: The prosthetic heart valve of Paragraph I, wherein the leaflet attachment panel spans approximately half the area of one entire cell.

Paragraph L: The prosthetic heart valve of Paragraph I, wherein the leaflet attachment panel spans approximately one-fourth the area of one entire cell.

Paragraph M: The prosthetic heart valve of Paragraph I, wherein the free edge forms a substantially straight line.

Paragraph N: The prosthetic heart valve of Paragraph I, wherein the free edge is curved.

Paragraph O: The prosthetic heart valve of Paragraph A, wherein the stent body includes an annulus section defining a first circumferential row of cells, an aortic section defining a second circumferential row of cells, and a third circumferential row of cells positioned between the first and second rows of cells.

Paragraph P: The prosthetic heart valve of Paragraph O, wherein the cell to which the leaflet attachment panel is attached is in the second circumferential row of cells.

Paragraph Q: The prosthetic heart valve of Paragraph O, wherein the cell to which the leaflet attachment panel is attached is in the third circumferential row of cells.

Paragraph R: A prosthetic heart valve, comprising: a stent body having a proximal end, a distal end, and including a plurality of cells arranged in a plurality of circumferential rows; cuff attached to the stent body; a leaflet attachment panel attached to at least one cell in one of the circumferential rows; a leaflet mounted to a portion of the leaflet attachment panel, the leaflet including a leaflet belly having a proximalmost point of attachment to the cuff; a reduced overlap area defined between the proximal end of the stent body and the proximalmost point of attachment of the leaflet belly to the cuff, the reduced overlap area having a size; wherein the size of the reduced overlap area is dependent upon (i) the circumferential row of cells the leaflet attachment panel is attached to and (ii) a position of the portion of the leaflet attachment panel to which the leaflet is mounted.

Paragraph S: The prosthetic heart valve of Paragraph R, wherein, when the leaflet is attached to a given portion of the leaflet attachment panel, the size of the reduced overlap area is greater when the leaflet attachment panel is attached to a relatively distal circumferential row of cells compared to when the leaflet attachment panel is attached to a relatively proximal circumferential row of cells.

Paragraph T: The prosthetic heart valve of Paragraph R, wherein, when the leaflet attachment panel is attached to a given circumferential row of cells, the size of the reduced overlap area is greater when the leaflet is attached to a relatively distal portion of the leaflet attachment panel compared to when the leaflet is attached to a relatively proximal portion of the leaflet attachment panel.

Paragraph U: A prosthetic heart valve, comprising: a stent body including a plurality of cells arranged in circumferential rows; a plurality of strut intersections being defined by an intersection of at least two adjacent cells; a cuff attached to the stent body; a portion of a first leaflet attached directly to one of the plurality of strut intersections; and a portion of a second leaflet attached directly to the one of the plurality of strut intersections.

Paragraph V: The prosthetic heart valve of Paragraph U, wherein the portions of the first and second leaflets are attached to the one strut intersection with a single suture.

Paragraph W: The prosthetic heart valve of Paragraph U, wherein the portions of the first and second leaflets are attached to the one strut intersection with a plurality of sutures.

Paragraph X: A prosthetic heart valve, comprising: a stent body having a proximal end and a distal end, the stent body formed from a plurality of open cells arranged in circumferential rows; a cuff attached to the stent body; a leaflet attachment panel attached to and overlying at least a portion of one of the open cells, the leaflet attachment panel having a proximal end and a distal end; and a leaflet attached to a portion of the leaflet attachment panel between the proximal end and the distal end thereof, the leaflet including a leaflet belly having a proximalmost point of attachment to the cuff, wherein an area between the proximal end of the stent body and the proximalmost point of attachment of the leaflet belly to the cuff defines a reduced overlap area having a longitudinal length; and wherein the longitudinal length of the reduced overlap area is at least dependent upon a location of attachment of the leaflet to the leaflet attachment panel between the proximal end and distal end thereof.

The invention claimed is:

1. A prosthetic heart valve, comprising:
a stent body including a plurality of cells arranged in circumferential rows, the plurality of cells including a first group of cells and a second group of cells, the stent body extending from an inflow end to an outflow end in a longitudinal direction;
a cuff sutured to the stent body;
at least one leaflet attachment panel sutured to the stent so that each cell in the first group of cells is at least partially covered by the at least one leaflet attachment panel and each cell in the second group of cells is fully uncovered by the at least one leaflet attachment panel, the at least one leaflet attachment panel being discontinuous with an adjacent leaflet attachment panel; and
at least one prosthetic valve element sutured to a single layer of the at least one leaflet attachment panel;
wherein the leaflet attachment panel is integral with none of the stent body, the cuff, and the prosthetic valve element;
wherein the cuff covers at least part of a luminal or abluminal surface of the stent body and a portion of the cuff is aligned with the at least one leaflet attachment panel in a radial direction transverse the longitudinal direction.

2. The prosthetic heart valve of claim 1, wherein the prosthetic valve element comprises a leaflet.

3. The prosthetic heart valve of claim 1, wherein the leaflet attachment panel is at least partially formed of fabric.

4. The prosthetic heart valve of claim 1, wherein the leaflet attachment panel is at least partially formed of tissue.

5. The prosthetic heart valve of claim 1, wherein the leaflet attachment panel spans an entire area of only one cell.

6. The prosthetic heart valve of claim 5, wherein the leaflet attachment panel spans more than the area of one entire cell.

7. The prosthetic heart valve of claim 1, wherein the leaflet attachment panel spans less than an area of one entire cell, the leaflet attachment panel having a free edge.

8. The prosthetic heart valve of claim 7, wherein the leaflet attachment panel spans approximately three-fourths the area of one entire cell.

9. The prosthetic heart valve of claim 7, wherein the leaflet attachment panel spans approximately half the area of one entire cell.

10. The prosthetic heart valve of claim 7, wherein the leaflet attachment panel spans approximately one-fourth the area of one entire cell.

11. The prosthetic heart valve of claim 7, wherein the free edge forms a substantially straight line.

12. The prosthetic heart valve of claim 7, wherein the free edge is curved.

13. The prosthetic heart valve of claim 1, wherein the stent body includes an annulus section defining a first circumferential row of cells, an aortic section defining a second circumferential row of cells, and a third circumferential row of cells positioned between the first and second rows of cells.

14. The prosthetic heart valve of claim 13, wherein the cell to which the leaflet attachment panel is attached is in the second circumferential row of cells.

15. The prosthetic heart valve of claim 13, wherein the cell to which the leaflet attachment panel is attached is in the third circumferential row of cells.

16. A prosthetic heart valve, comprising:
a stent body extending in a longitudinal direction from an inflow end at a proximal end of the stent body to an outflow end at a distal end of the stent body, and including a plurality of cells arranged in a plurality of circumferential rows;
a cuff sutured to the stent body and covering at least part of a luminal or abluminal surface of the stent body;

a leaflet attachment panel sutured to at least one cell in one of the circumferential rows and spanning an entire area of only one cell;
a leaflet sutured to a single layer of the leaflet attachment panel, the leaflet including a leaflet belly having a proximalmost point of attachment to the cuff;
a reduced overlap area defined between the proximal end of the stent body and the proximalmost point of attachment of the leaflet belly to the cuff, the reduced overlap area having a size;
wherein the size of the reduced overlap area is dependent upon (i) the circumferential row of cells the leaflet attachment panel is attached to and (ii) a position of the portion of the leaflet attachment panel to which the leaflet is mounted;
wherein the leaflet attachment panel is integral with none of the stent body, the cuff and the leaflet, and a portion of the cuff is aligned with the leaflet attachment panel in a radial direction transverse the longitudinal direction.

17. The prosthetic heart valve of claim 16, wherein, when the leaflet is attached to a given portion of the leaflet attachment panel, the size of the reduced overlap area is greater when the leaflet attachment panel is attached to a relatively distal circumferential row of cells compared to when the leaflet attachment panel is attached to a relatively proximal circumferential row of cells.

18. The prosthetic heart valve of claim 16, wherein, when the leaflet attachment panel is attached to a given circumferential row of cells, the size of the reduced overlap area is greater when the leaflet is attached to a relatively distal portion of the leaflet attachment panel compared to when the leaflet is attached to a relatively proximal portion of the leaflet attachment panel.

19. A prosthetic heart valve, comprising:
a stent body extending in a longitudinal direction from an inflow end at a proximal end of the stent body to an outflow end at a distal end of the stent body, the stent body being formed from a plurality of open cells arranged in circumferential rows;
a cuff sutured to the stent body and covering at least part of a luminal or abluminal surface of the stent body;
a leaflet attachment panel sutured to and overlying at least a portion of one of the open cells and spanning an entire area of only one cell, the leaflet attachment panel having a proximal end and a distal end; and
a leaflet sutured to a single layer of the leaflet attachment panel between the proximal end and the distal end thereof, the leaflet including a leaflet belly having a proximalmost point of attachment to the cuff,
wherein an area between the proximal end of the stent body and the proximalmost point of attachment of the leaflet belly to the cuff defines a reduced overlap area having a longitudinal length;
wherein the longitudinal length of the reduced overlap area is dependent at least upon a location of attachment of the leaflet to the leaflet attachment panel between the proximal end and distal end thereof; and
wherein the leaflet attachment panel is integral with none of the stent body, the cuff and the leaflet, and a portion of the cuff is aligned with the leaflet attachment panel in a radial direction transverse the longitudinal direction.

20. The prosthetic heart valve of claim 1, wherein the cuff is formed of a biological material.

21. The prosthetic heart valve of claim 1, wherein the cuff is formed of a polymer.

* * * * *